US012788442B2

(12) United States Patent
Alambeigi et al.

(10) Patent No.: US 12,788,442 B2
(45) Date of Patent: Nov. 10, 2026

(54) FLEXIBLE IMPLANTS AND METHODS OF ENHANCED BONE FIXATION

(71) Applicant: Board of Regents, The University of Texas System, Austin, TX (US)

(72) Inventors: Farshid Alambeigi, Austin, TX (US); Amir Hossein Eskandari Shahrabi, Montreal (CA); Alexander Cohen, Austin, TX (US); Jordan Amadio, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 48 days.

(21) Appl. No.: 18/437,843

(22) Filed: Feb. 9, 2024

(65) Prior Publication Data

US 2024/0277378 A1 Aug. 22, 2024

Related U.S. Application Data

(63) Continuation of application No. 18/264,125, filed as application No. PCT/US2022/015060 on Feb. 3, 2022.

(Continued)

(51) Int. Cl.
*A61B 17/70* (2006.01)
*A61B 17/86* (2006.01)

(Continued)

(52) U.S. Cl.
CPC ...... *A61B 17/7035* (2013.01); *A61B 17/8625* (2013.01); *A61F 2/28* (2013.01); *A61F 2/30* (2013.01); *A61F 2002/3011* (2013.01)

(58) Field of Classification Search
CPC . A61B 17/865; A61B 17/8625; A61B 17/863; A61B 17/864; A61B 17/70;

(Continued)

(56) References Cited

U.S. PATENT DOCUMENTS 4,318,651 A * 3/1982 Ragen ...................... F16B 37/12 411/392
4,762,453 A * 8/1988 DeCaro ............... F16B 25/0005 411/383

(Continued)

FOREIGN PATENT DOCUMENTS

DE 908906 C 4/1954
DE 202014003640 U1 5/2014

(Continued)

OTHER PUBLICATIONS

"Raising awareness to strengthen bone health: 2018 annual report." National Osteoporosis Foundation (NOF). [Online]. Available: http://www.bonehealthandosteoporosis.org/wpcontent/uploads/2018NOFAnnualreportFINAL.pdf.

(Continued)

*Primary Examiner* — Ellen C Hammond
(74) *Attorney, Agent, or Firm* — Riverside Law LLP

(57) ABSTRACT

The present invention provides methods of forming flexible implant devices and U-bridge implants that drive into curved trajectories to enhance implant fixation in bone. The curved drilling trajectories avoid regions of low bone mineral density, such that flexible implants and/or U-bridge implants driven into the curved drilling trajectories are anchored in regions of high bone mineral density to improve the stability of bone fixation. The flexible implants and U-bridge implants are suitable for several applications, including but not limited to spinal fixation, orthopedic bone fixation, and neurosurgery.

13 Claims, 39 Drawing Sheets

Related U.S. Application Data

(60) Provisional application No. 63/145,067, filed on Feb. 3, 2021, provisional application No. 63/145,054, filed on Feb. 3, 2021.

(51) Int. Cl.
*A61F 2/28* (2006.01)
*A61F 2/30* (2006.01)

(58) Field of Classification Search
CPC ............ A61B 17/7053; A61B 17/7062; A61B 17/7064; A61B 17/7065; A61B 2017/8655
See application file for complete search history.

(56) References Cited

U.S. PATENT DOCUMENTS

| | | | | |
|---|---|---|---|---|
| 4,959,064 | A | 9/1990 | Engelhardt | |
| 8,317,845 | B2 * | 11/2012 | Stinnette | A61B 17/8685 606/264 |
| 8,740,955 | B2 | 6/2014 | Bottlang | |
| 9,498,264 | B2 | 11/2016 | Harshman | |
| 9,579,188 | B2 * | 2/2017 | Bowman | A61B 17/0401 |
| 9,839,435 | B2 | 12/2017 | Meek | |
| 10,258,394 | B2 | 4/2019 | Harshman | |
| 10,307,188 | B2 | 6/2019 | Harshman | |
| 10,492,838 | B2 | 12/2019 | Fallin | |
| 10,973,559 | B2 | 4/2021 | Harshman | |
| 11,369,421 | B2 | 6/2022 | Harshman | |
| 11,419,645 | B2 | 8/2022 | Stinson | |
| 11,529,148 | B2 | 12/2022 | Meek | |
| 11,832,856 | B2 | 12/2023 | Meek | |
| 12,023,074 | B2 | 7/2024 | Harshman | |
| 12,295,623 | B1 * | 5/2025 | Hynes | A61B 17/7055 |
| 2003/0229350 | A1 * | 12/2003 | Kay | A61B 17/86 470/10 |
| 2005/0125066 | A1 * | 6/2005 | McAfee | A61F 2/4611 623/908 |
| 2008/0306536 | A1 | 12/2008 | Frigg | |
| 2010/0305700 | A1 * | 12/2010 | Ben-Arye | A61B 17/70 606/279 |
| 2011/0295319 | A1 | 12/2011 | Duplessis | |
| 2012/0232597 | A1 * | 9/2012 | Saidha | A61B 17/869 606/86 R |
| 2013/0253594 | A1 * | 9/2013 | Zucherman | A61B 17/863 606/305 |
| 2017/0014170 | A1 | 1/2017 | Fallin | |
| 2022/0175432 | A1 * | 6/2022 | Shen | A61B 17/869 |
| 2022/0175433 | A1 * | 6/2022 | Kuntz | A61B 17/7055 |

FOREIGN PATENT DOCUMENTS

| | | |
|---|---|---|
| EP | 0374088 | 6/1990 |
| EP | 3402423 B1 | 4/2025 |

OTHER PUBLICATIONS

C. Klotzbuecher, P. Ross, P. Landsman, T. Abbott III, and M. Berger, "Patients with prior fractures have an increased risk of future fractures: a summary of the literature and statistical synthesis," Journal of bone and mineral research, vol. 15, No. 4, pp. 721-739, 2000.
C. L. Goldstein, D. S. Brodke, and T. J. Choma, "Surgical management of spinal conditions in the elderly osteoporotic spine," Neurosurgery, vol. 77, No. suppl 1, pp. S98-S107, 2015.
E. L et al., "Healthcare policy changes in osteoporosis can improve outcomes and reduce costs in the united states," JBMR plus, vol. 3, No. 9, 2019.
F. Alambeigi, "Dexterity and autonomy in minimally invasive surgical robotics intervention," Ph.D. dissertation, John Hopkins University, 2019.
F. Alambeigi, M. Bakhtiarinejad, A. Azizi, R. Hegeman, I. lordachita, H. Khanuja, and M. Armand, "Inroads toward robot-assisted internal fixation of bone fractures using a bendable medical screw and the curved drilling technique," in 2018 7th IEEE International Conference on Biomedical Robotics and Biomechatronics (Biorob). IEEE, 2018, pp. 595-600.
F. Alambeigi, M. Bakhtiarinejad, S. Sefati, R. Hegeman, I. lordachita, H. Khanuja, and M. Armand, "On the use of a continuum manipulator and a bendable medical screw for minimally invasive interventions in orthopedic surgery," IEEE transactions on medical robotics and bionics, vol. 1, No. 1, pp. 14-21, 2019.
F. Shweikeh, J. P. Amadio, M. Arnell, Z. R. Barnard, T. T. Kim, J. P. Johnson, and D. Drazin, "robotics and the spine: a review of current and ongoing applications," Neurosurgical Focus, vol. 36, No. 3, p. E10, 2014.
G. F. Anderson and p. S. Hussey, "Population aging: A comparison among industrialized countries: Populations around the world are growing older, but the trends are not cause for despair." Health affairs, vol. 19, No. 3, pp. 191-203, 2000.
L. Melton III, E. Atkinson, C. Cooper, W. O'Fallon, and B. Riggs, "Vertebralfractures predict subsequent fractures," Osteoporosis International, vol. 10, No. 3, pp. 214-221, 1999.
M. Nevitt, B. Ettinger, D. Black, K. Stone, S. Jamal, K. Ensrud, M. Segal, H. Genant, and S. Cummings, "The association of radiographically detected vertebral fractures with back pain and function: a prospective study."
M. Tilton, G. S. Lewis, H. B. Wee, A. Armstrong, M. W. Hast, and G. Manogharan, "Additive manufacturing of fracture fixation implants: Design, material characterization, biomechanical modeling and experimentation," Additive Manufacturing, vol. 33, 2020.
N. C. Wright, A. C. Looker, K. G. Saag, J. R. Curtis, E. S. Delzell, S. Randall, and B. Dawson-Hughes, "The recent prevalence of osteoporosis and low bone mass in the united states based on bone mineral density at the femoral neck or lumbar spine," Journal of Bone and Mineral Research, vol. 29, No. 11, pp. 2520-2526, 2014.
Osteoporosis fast facts. [Online]. Available: www.nof.org.
P. Lips, C. Cooper, D. Agnusdei, F. Caulin, P. Egger, O. Johnell, J. Kanis, S. Kellingray, A. Leplege, U. Liberman, E. McCloskey, H. Minne, J. Reeve, J. Reginster, M. Scholz, C. Todd, and M. de Vernejoul, "Quality of life in patients with vertebral fractures: validation of the quality of life questionnaire of the european foundation for osteoporosis (qualeffo). working party for quality of life of the european foundation for osteoporosis."
R. Burge, B. Dawson-Hughes, D. H. Solomon, J. B. Wong, A. King, and A. Tosteson, "Incidence and economic burden of osteoporosis-related fractures in the united states, 2005-2025," Journal of bone and mineral research, vol. 22, No. 3, pp. 465-475, 2007.
R. Feng, "Material characterization of additive manufactured metals using a line-focus transducer system," Master's thesis, University of Pittsburgh, 2021.
S. Pluijm, M. Dik, C. Jonker, D. Deeg, G. Van Kamp, and P. Lips, "Effects of gender and age on the association of apolipoprotein e ϵ4 with bone mineral density, bone turnover and the risk of fractures in older people," Osteoporosis International, vol. 13, No. 9, pp. 701-709, 2002.
T. M. Shea, J. Laun, S. A. Gonzalez-Blohm, J. J. Doulgeris, W. E. Lee 3rd, K. Aghayev, and F. D. Vrionis, "Designs and techniques that improve the pullout strength of pedicle screws in osteoporotic vertebrae: current status," BioMed research international, 2014.
Office Action (Final Rejection) dated Mar. 13, 2026 for U.S. Appl. No. 18/264,125 (pp. 1-11).

* cited by examiner

FLEXIBLE IMPLANTS AND METHODS OF ENHANCED BONE FIXATION

CROSS-REFERENCE TO RELATED APPLICATIONS

This application is a Continuation of U.S. patent application Ser. No. 18/264,125, filed Aug. 3, 2023, which is a U.S. national phase application filed under 35 U.S.C. § 371 claiming benefit to International Patent Application No. PCT/US2022/015060, filed Feb. 3, 2022, which is entitled to priority of U.S. Provisional Patent Application No. 63/145,067 filed on Feb. 3, 2021, and to U.S. Provisional Application No. 63/145,054 filed on Feb. 3, 2021, the contents of which are each incorporated by reference herein in their entirety.

STATEMENT REGARDING FEDERALLY SPONSORED RESEARCH OR DEVELOPMENT

This invention was made with government support under Grant No. R21 EB030796 awarded by the National Institutes of Health. The government has certain rights in the invention.

BACKGROUND OF THE INVENTION

Screw implants are commonly used to stabilize bone fractures, reconstruct bone after tumor resection or destruction from infection, and treat congenital and acquired degenerative diseases. Screw fixation usually inserts rigid bone screws through strong cortical bone and into the more porous cancellous bone. The screws can then be rigidly connected with locking rods to ideally provide a stable fixation and load sharing feature before a robust bone fusion or healing occurs. However, screw fixation suffers from various types of complications and failures, including but not limited to screw misplacement, screw fracture, bone fracture, and loosening and pullout of screw implants. In particular, while loosening and pullout of screw implants is a prevalent problem in osteoporotic bone, it is also a common occurrence in bones with normal and healthy bone mineral density (BMD).

The reasons for the inadequacy of screw implants in bone are manifold. Screw implant sites in bone must deal with narrow and confined anatomical constraints, limiting the angles of approach for the screws. Nerves and blood vessels also must be avoided from the screw path. Additional obstacles are regions of low BMD. Fixation strength and quality of screw implant fixation directly depend on the BMD of an implant site. Traditional drilling instruments and screws are rigid and lack the sufficient dexterity to navigate the aforementioned anatomical constraints, limiting implant trajectories to linear paths that often lead to screw misplacement and nerve injury and necessarily cross low BMD regions.

Thus, there is a need in the art for improved devices and methods for implant fixation in bone that are adapted for a subject's bone mineral density. The present invention meets this need.

SUMMARY OF THE INVENTION

In one aspect, the present invention relates to a flexible implant device, comprising: a length extending between a proximal end and a distal end; a screw head at the proximal end; a rigid shank extending from the screw head towards the distal end for a portion of the length; and a flexible shank-less engagement member at the distal end. In one embodiment, the engagement member extends from a distal end of the shank. In one embodiment, the engagement member is partially attached to an exterior of the shank. In one embodiment, the engagement member extends from the screw head. In one embodiment, the engagement member comprises a variable cross-sectional shape. In one embodiment, the cross-sectional shape is selected from the group consisting of: a triangle shape, a square shape, a pentagon shape, a hexagon shape, a rectangular shape, a rhombus shape, a diamond shape, and a trapezoid shape. In one embodiment, the engagement member has an outer diameter that is variable along the length of the engagement member. In one embodiment, the engagement member has an inner diameter that is variable along the length of the engagement member.

In one embodiment, the distal end of the engagement member comprises a self-tapping tip. In one embodiment, the distal end of the engagement member comprises a tip configured to mate to a screw head of a flexible implant device, wherein the tip comprises a mating connector selected from the group consisting of: a push lock fitting, a threaded connector, and a magnet.

In one embodiment, the engagement member comprises an engagement structure on an outer-facing surface selected from the group consisting of: a screw thread, a knurling pattern, a grating pattern, and combinations thereof. In one embodiment, the screw thread has a thread pitch that is variable along the length of the screw thread.

In one aspect, the present invention relates to a U-bridge implant device comprising: a length extending between a proximal end and a distal end; a driving head at the proximal end; a mating connector at the distal end; and a flexible engagement member positioned between the driving head and the mating connector.

In one embodiment, the engagement member is attached to the driving head at the proximal end and the mating connector at the distal end, such that the engagement member extends for the length of the implant device. In one embodiment, the driving head is attached to a shank that extends towards the distal end for a portion of the length of the implant device. In one embodiment, the length of the implant device comprising the shank is rigid. In one embodiment, the engagement member attaches to an exterior of the shank for at least a portion of a length of the shank. In one embodiment, the engagement member extends from the shank at a proximal end and is attached to the mating connector at a distal end. In one embodiment, the mating connector is selected from the group consisting of: a push lock fitting, a threaded connector, and a magnet. In one embodiment, the engagement member comprises a variable cross-sectional shape. In one embodiment, the cross-sectional shape is selected from the group consisting of: a triangle shape, a square shape, a pentagon shape, a hexagon shape, a rectangular shape, a rhombus shape, a diamond shape, and a trapezoid shape.

In one embodiment, the engagement member has an outer diameter that is variable along the length of the engagement member. In one embodiment, the engagement member has an inner diameter that is variable along the length of the engagement member. In one embodiment, the engagement member comprises an engagement structure on an outer-facing surface selected from the group consisting of: a screw thread, a knurling pattern, a grating pattern, and combinations thereof. In one embodiment, the screw thread has a thread pitch that is variable along the length of the screw thread.

In one aspect, the present invention relates to a U-bridge implant system comprising: at least one first U-bridge implant device comprising a length extending between a driving head at a proximal end and a mating connector at a distal end; and at least one second U-bridge implant device comprising a length extending between a driving head at a proximal end and a mating connector at a distal end; wherein the mating connector of the first U-bridge implant device is mated to the mating connector of the second U-bridge implant device.

In one embodiment, an engagement member of the first U-bridge implant device is attached to the driving head of the first U-bridge implant device at the proximal end and the mating connector of the first U-bridge implant device at the distal end, and wherein an engagement member of the second U-bridge implant device is attached to the driving head of the second U-bridge implant device at the proximal end and the mating connector of the second U-bridge implant device at the distal end, such that the engagement member of each of the first and second U-bridge implant device extends for the length of each of the first and second U-bridge implant device, respectively.

In one embodiment, the driving head of each of the first and second U-bridge implant device is attached to a shank that extends towards the distal end of each of the first and second U-bridge implant device for a portion of the length of each of the first and second U-bridge implant device, respectively.

In one embodiment, the length of each of the first and second U-bridge implant device comprising the shank is rigid. In one embodiment, the engagement member of each of the first and second U-bridge implant device attaches to an exterior of the shank of each of the first and second U-bridge implant device for at least a portion of a length of the shank of each of the first and second U-bridge implant device.

In one embodiment, the engagement member of each of the first and second U-bridge implant device extends from the shank of each of the first and second U-bridge implant device at a proximal end and is attached to the mating connector of each of the first and second U-bridge implant device at a distal end. In one embodiment, the mating connector of each of the first and second U-bridge implant device is selected from the group consisting of: a push lock fitting, a threaded connector, and a magnet.

In one aspect, the present invention relates to a method of forming a custom flexible implant device or U-bridge implant device specific to a subject, comprising the steps of: characterizing a target bone tissue of the subject, such that regions of osteoporotic bone or regions of bone with low mineral density are identified in the target bone tissue; forming an implant trajectory in the target bone tissue that avoids the regions of osteoporotic bone and regions of bone with low mineral density; and fabricating a flexible implant device or a U-bridge implant device configured to conform to the implant trajectory in the target bone.

In one embodiment, the step of characterizing the target bone tissue comprises the steps of: performing one or more quantitative computed tomography (QCT) scans on the target bone tissue; converting the one or more QCT scans into a three-dimensional finite element model of the target bone tissue; and demarcating osteoporotic regions or low bone mineral density regions in the three-dimensional finite element model.

In one embodiment, the fabrication step modifies one or more of: shank length, engagement member length, engagement member outer diameter, engagement member inner diameter, engagement member cross-sectional shape, and tip. In one embodiment, the engagement member is a screw thread, such that the fabrication step modifies screw thread pitch. In one embodiment, the implant trajectory extends into an adjacent cortical bone.

BRIEF DESCRIPTION OF THE DRAWINGS

The following detailed description of exemplary embodiments of the invention will be better understood when read in conjunction with the appended drawings. It should be understood, however, that the invention is not limited to the precise arrangements and instrumentalities of the embodiments shown in the drawings.

FIG. 1A shows a traditional vertebral fixation using pedicle screws (left) and the inability to avoid weak regions of bone (right). FIG. 1B shows additional drawbacks to traditional pedicle screws, wherein the rectangle demonstrates the constrained access channels used typically for implanting rigid pedicle screws (left) and the mechanism by which traditional pedicle screws loosen over time where the fulcrum effect in a pedicle screw results in maximum stress occurring in two separate regions and causing loosening propagation in an hourglass pattern (right). FIG. 1C compares the dexterity of a curving drilling instrument forming a curved drilling trajectory contained within high bone mineral density regions versus a traditional drilling instrument with a rigid drill bit in low bone mineral density regions (left), wherein a flexible implant device or a U-bridge implant can fit within a curved trajectory that a traditional pedicle screw cannot (right). FIG. 1D shows the insertion and combining of a U-bridge implant (left) and the stress distribution of the implanted U-bridge implant, wherein exerted external loads are distributed along a large continuous surface (right).

FIG. 6A shows a U-bridge implant having a shank (top) and not having a shank (bottom).

FIG. 6B shows a U-bridge implant having screw heads adapted for spinal fixation as pedicle screws.

FIG. 7A shows a U-bridge implant device before implanting (top) and after implanting into a vertebra (bottom). FIG. 74B shows a series of U-bridge implant devices implanted into a spine.

Figures 8A, 8B, 8C:
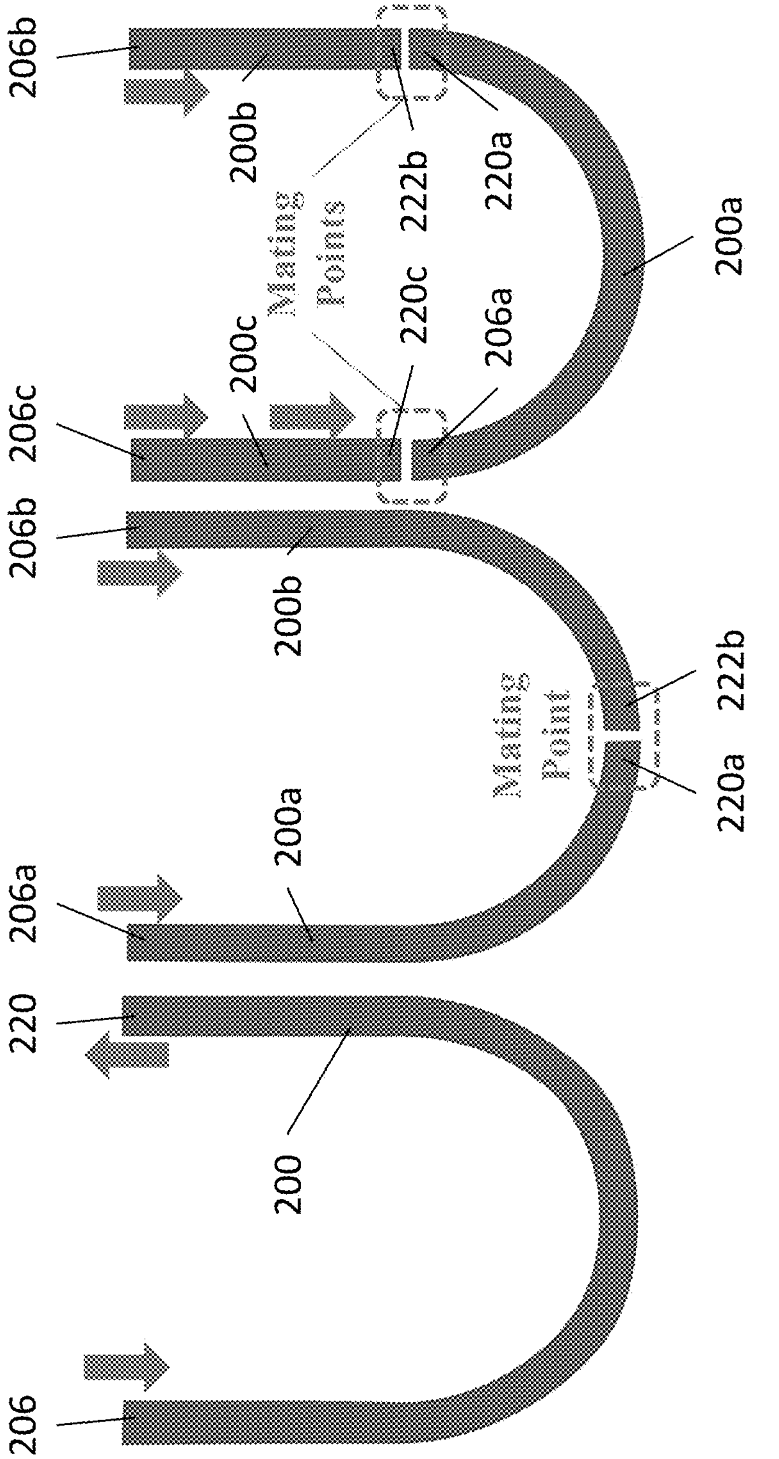
FIG. 8A through FIG. 8C depict diagrams of exemplary U-bridge implant devices of varying lengths. U-bridge implant devices can be used as solitary implants (FIG. 8A)

or joined together from two or more devices (FIG. 8B, FIG. 8C). The arrows show the direction of implant insertion.

Figure 9:
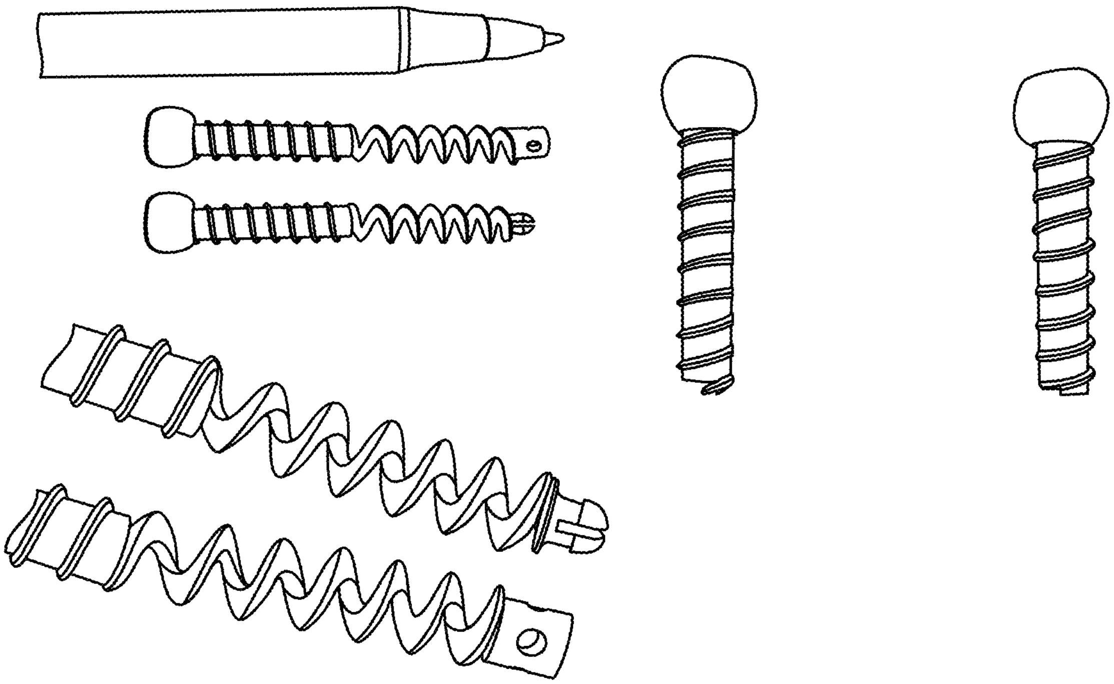

FIG. 9 depicts an exemplary U-bridge implant constructed from steel.

Figure 10A:
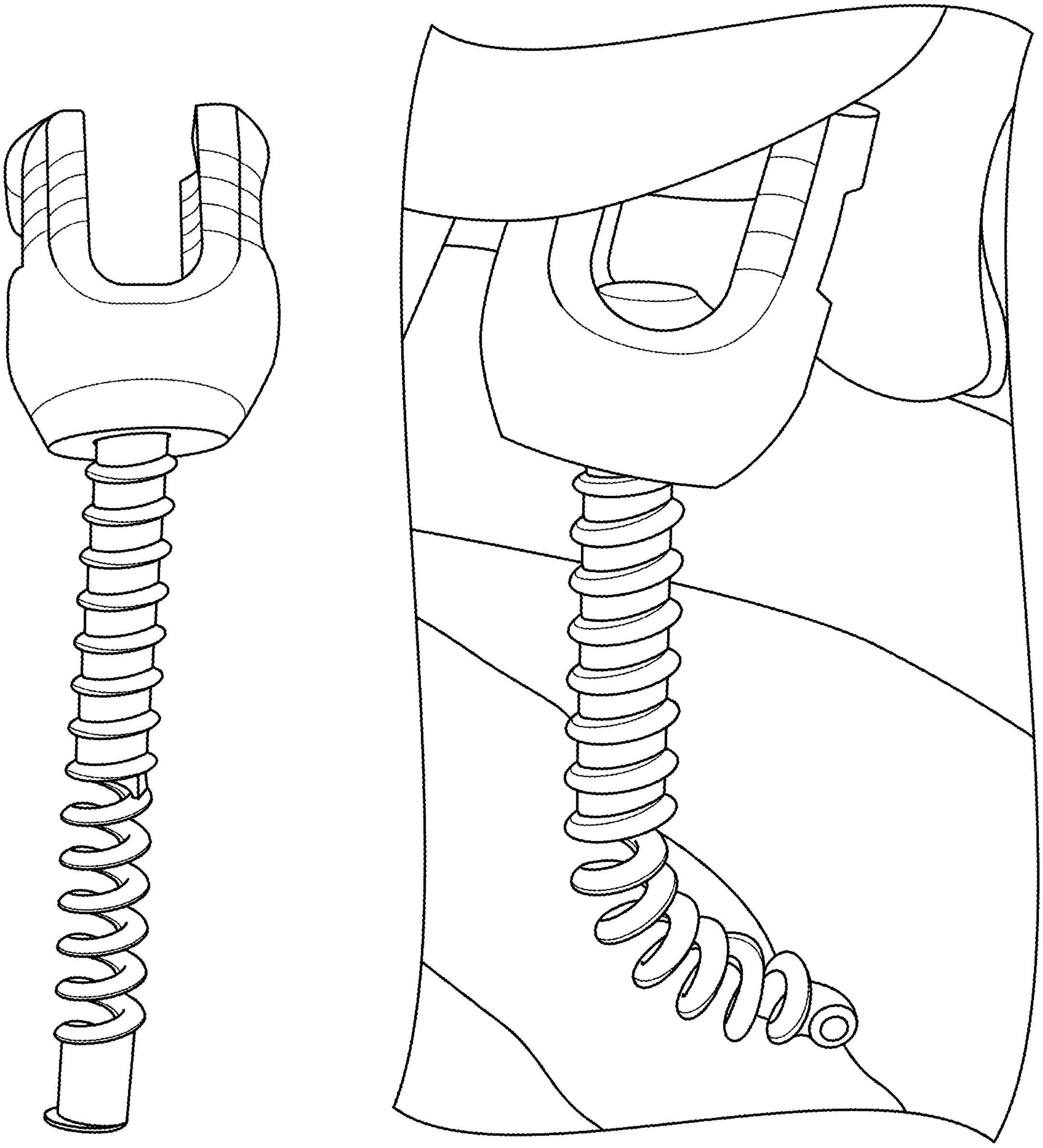
Figure 10B:
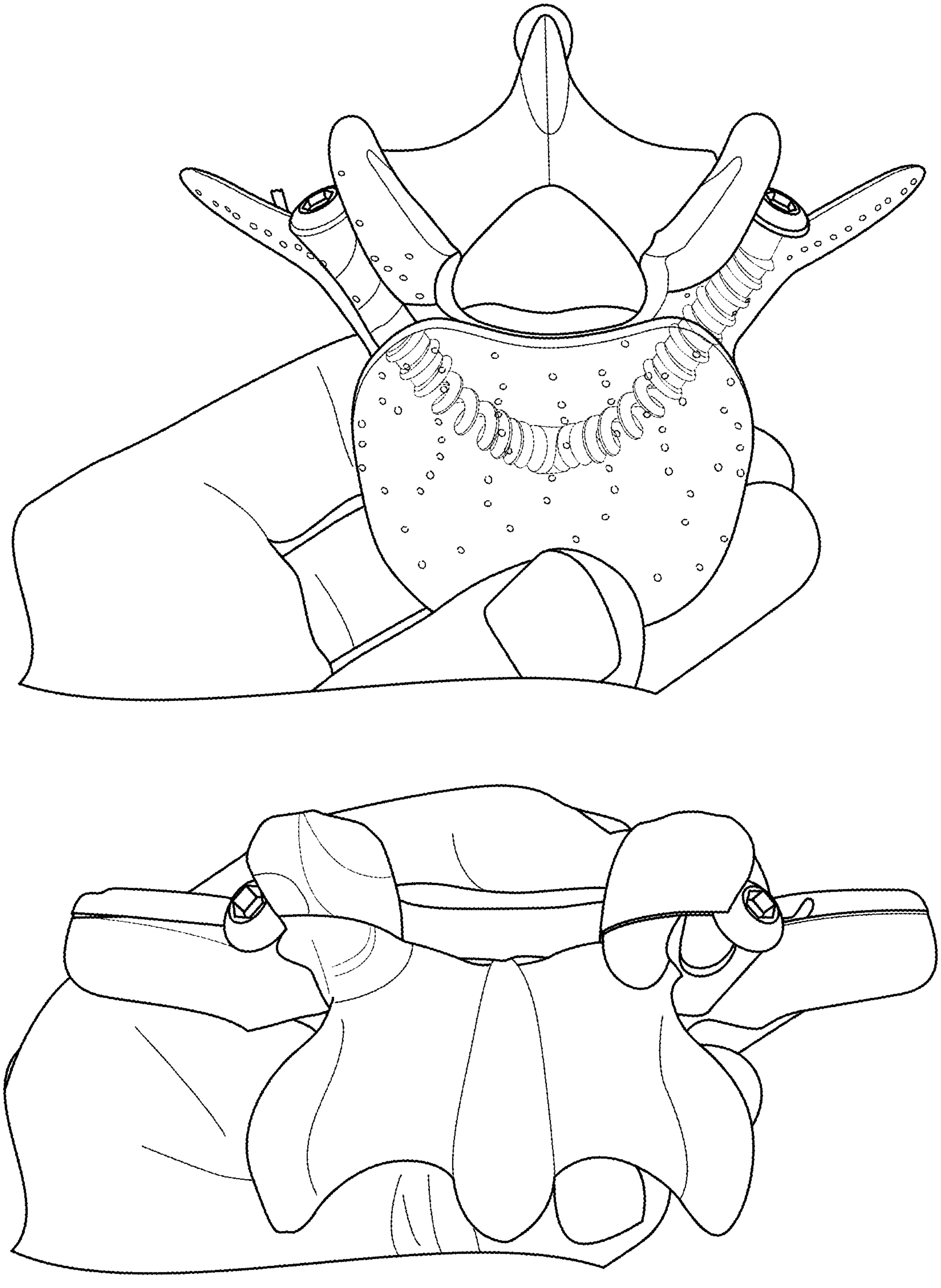
Figure 10C:
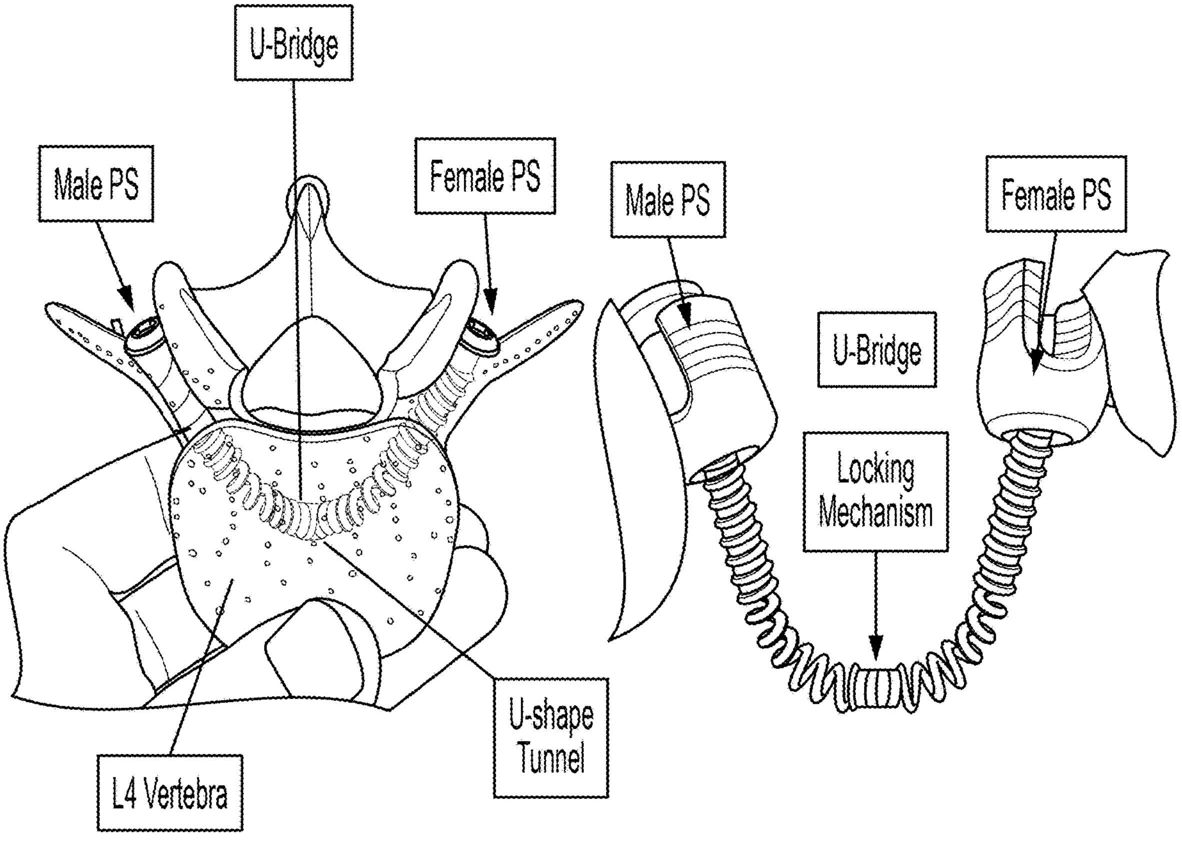

FIG. 10A through FIG. 10C depicts prototype U-bridge implant devices.

FIG. 10A depicts a 3D printed U-bridge implant device, demonstrating flexibility. FIG. 10B depicts a 3D printed U-bridge device implanted into a model vertebra. FIG. 10C depicts annotations images of a 3D printed U-bridge implant device and model vertebra.

Figure 11:
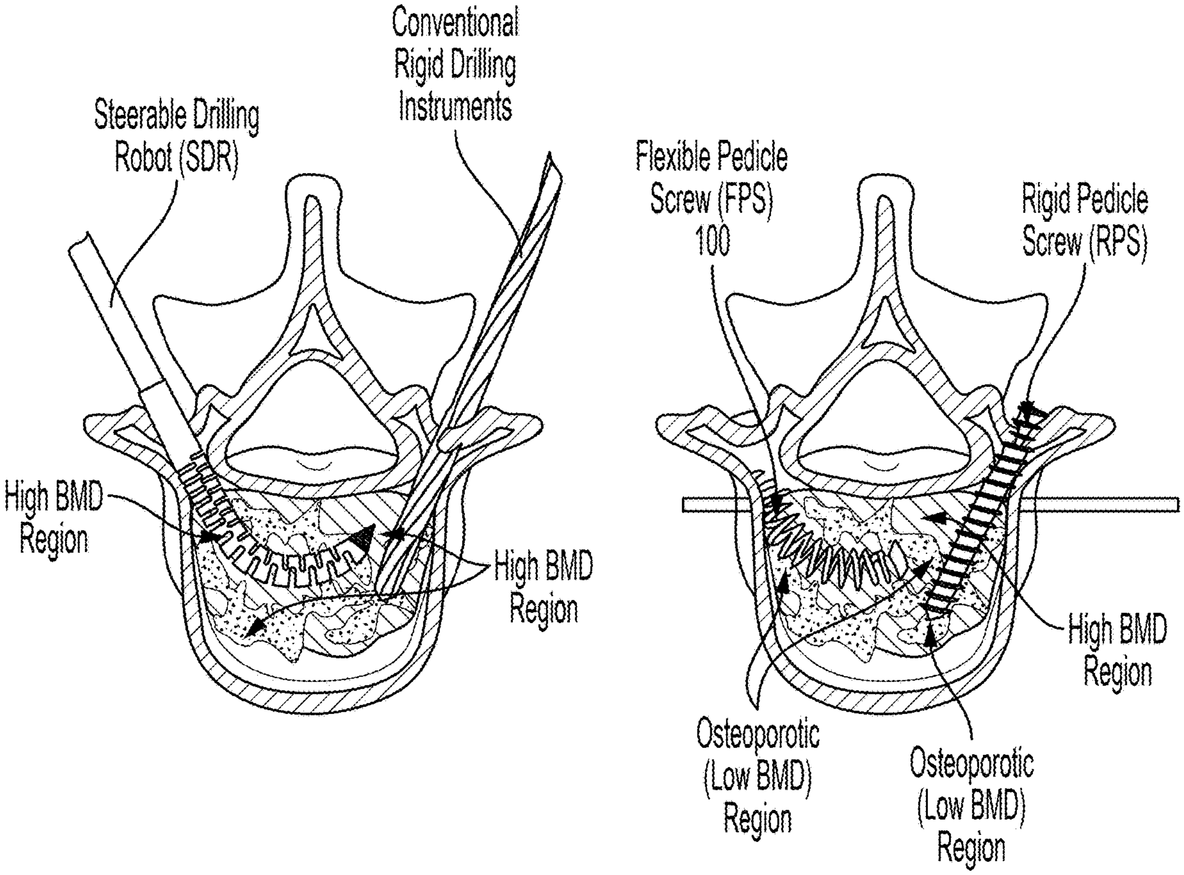

FIG. 11 depicts a schematic of an osteoporotic vertebra cross-section comparing flexible and rigid drilling (left) and flexible and rigid screws (right). The vertebra cross-section reveals regions of high bone mineral density and low bone mineral density. A conventional rigid drill and screw have limited angles of approach and may be driven into regions of low bone mineral density, leading to low pullout strength and high chance of failure. A flexible drill and screw are capable of specifically targeting regions of high bone mineral density and avoiding regions of low bone mineral density to maximize screw pullout strength.

Figure 12:
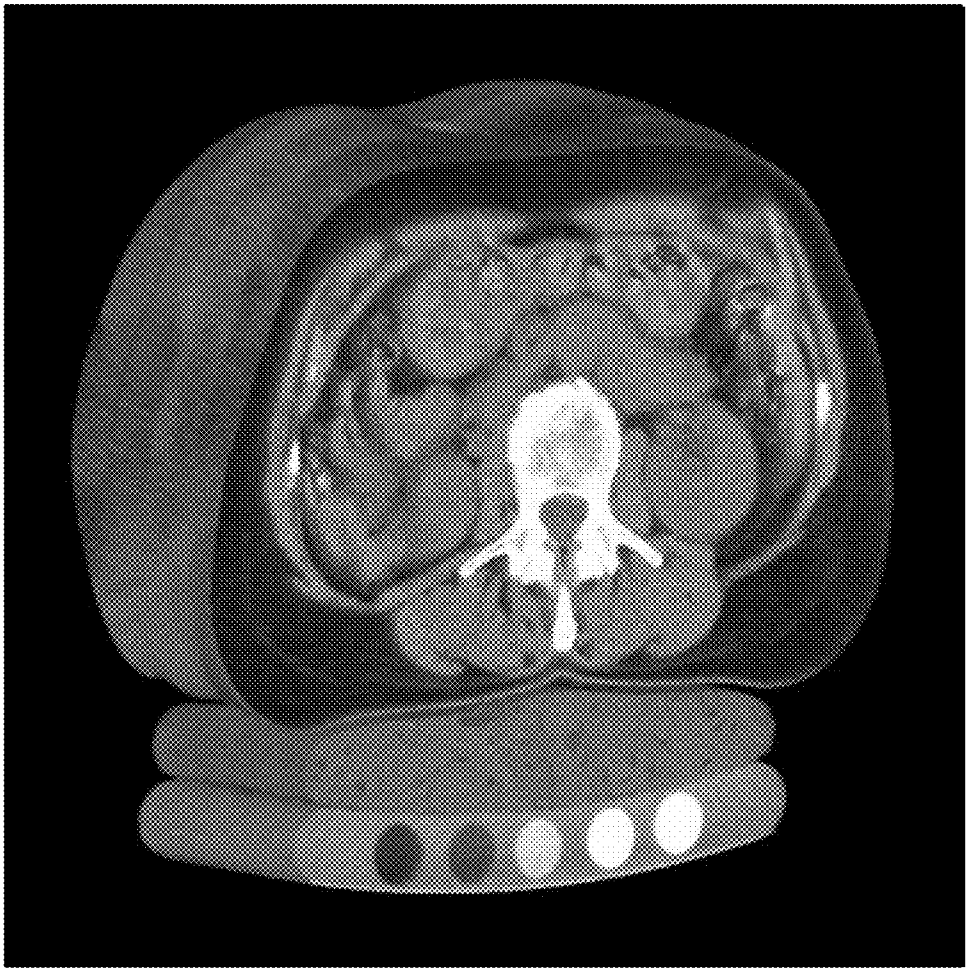

FIG. 12 depicts the results of a quantitative computed tomography scan on a subject's vertebra (middle) and a calibration phantom (bottom), wherein regions of high density are lighter in color and regions of low density are darker in color. Bone mineral density values can be quantified by converting Hounsfield Units of the image.

Figure 13:
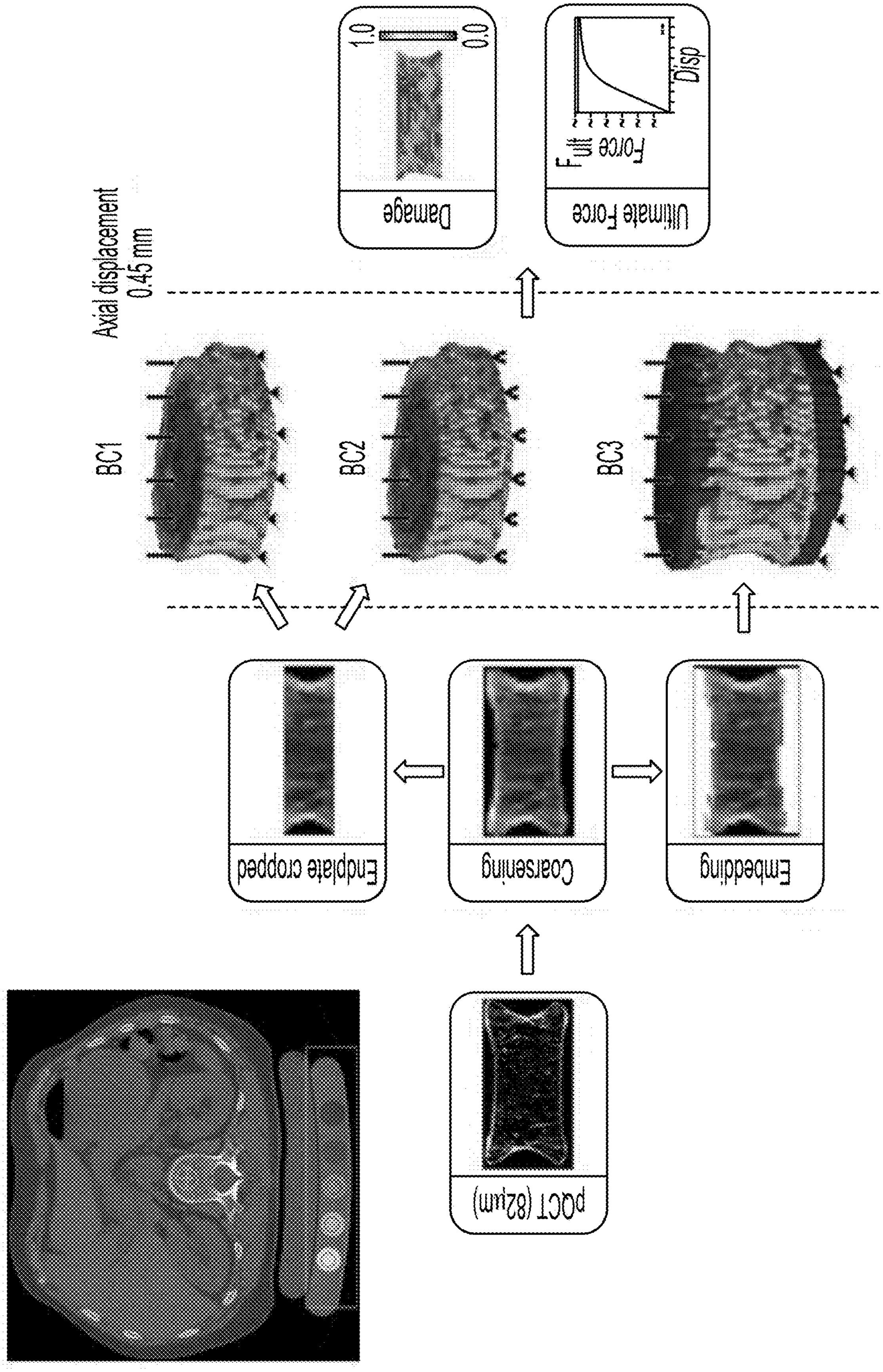

FIG. 13 depicts a schematic of a workflow converting a quantitative computed tomography scan of a subject's vertebra into a biomechanical model. The scanned image is coarsened and converted to a three-dimensional voxel finite element model, wherein each voxel corresponds to the density of a region of the scanned image.

Figure 14:
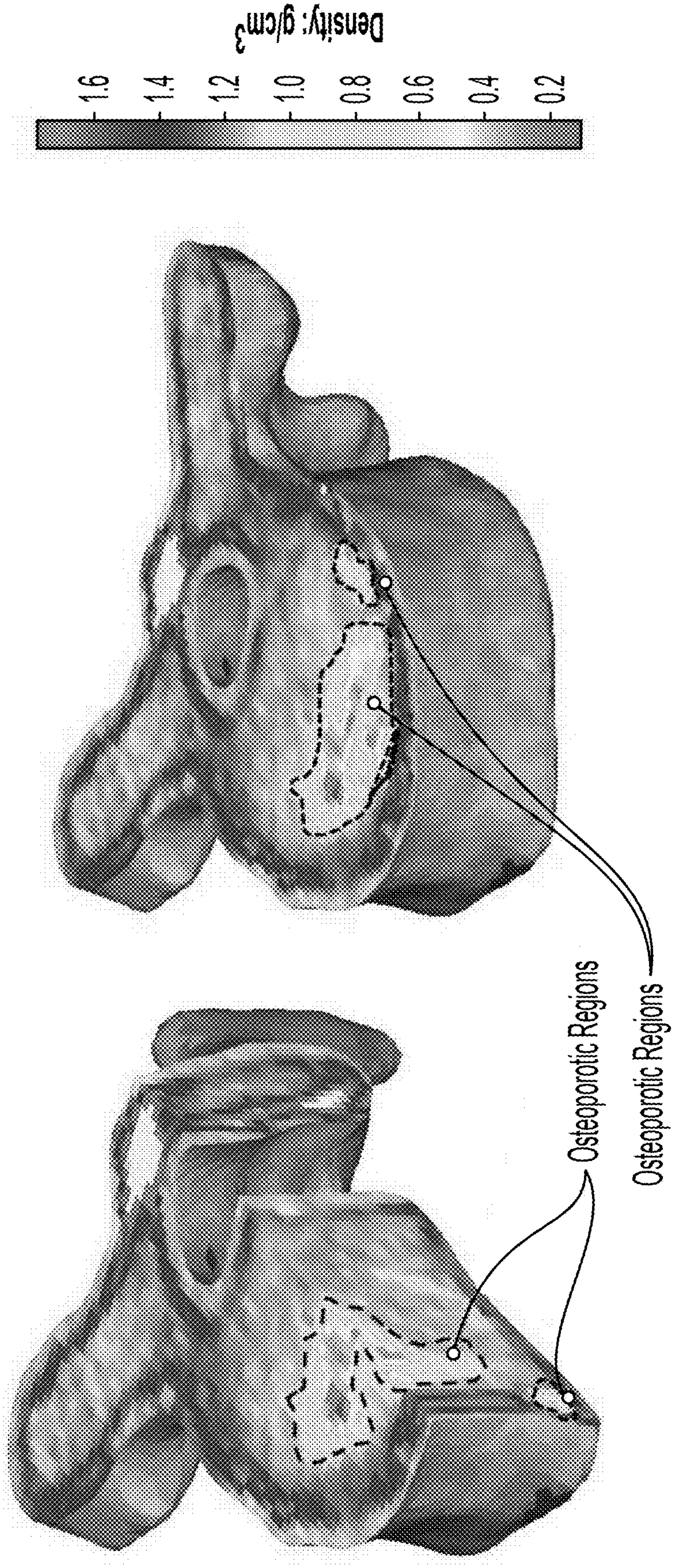

FIG. 14 depicts a schematic of a three-dimensional finite element model of a vertebra, wherein osteoporotic regions are characterized and defined. Here, the threshold for osteoporotic regions is a density of less than 80 mg/cm$^3$.

Figure 15:
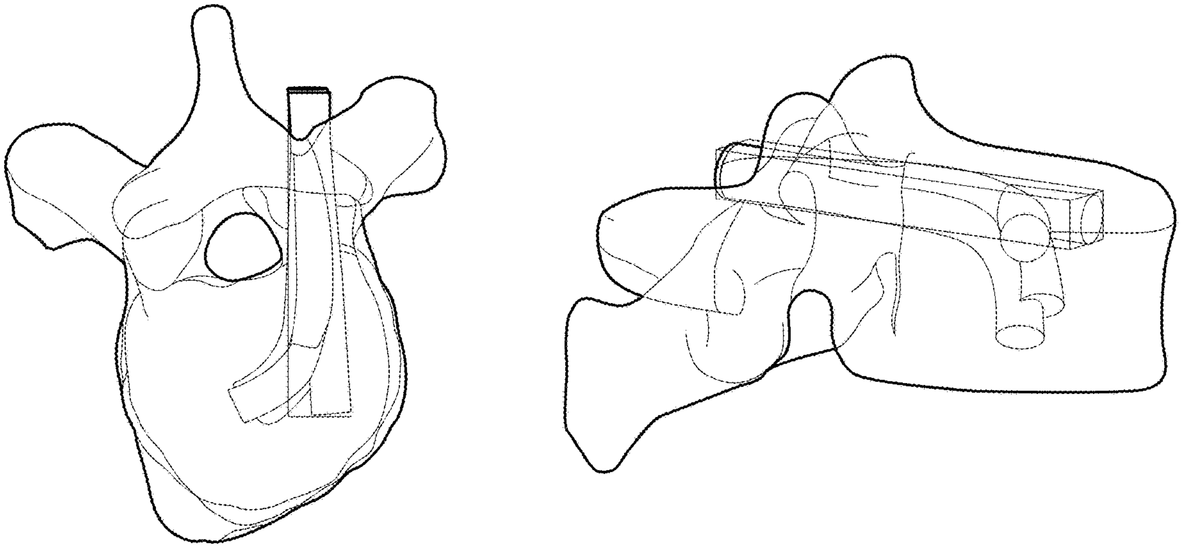

FIG. 15 depicts a schematic of a three-dimensional model of a vertebra and a plurality of flexible implant trajectories angled to avoid regions of low bone mineral density.

Figure 16:
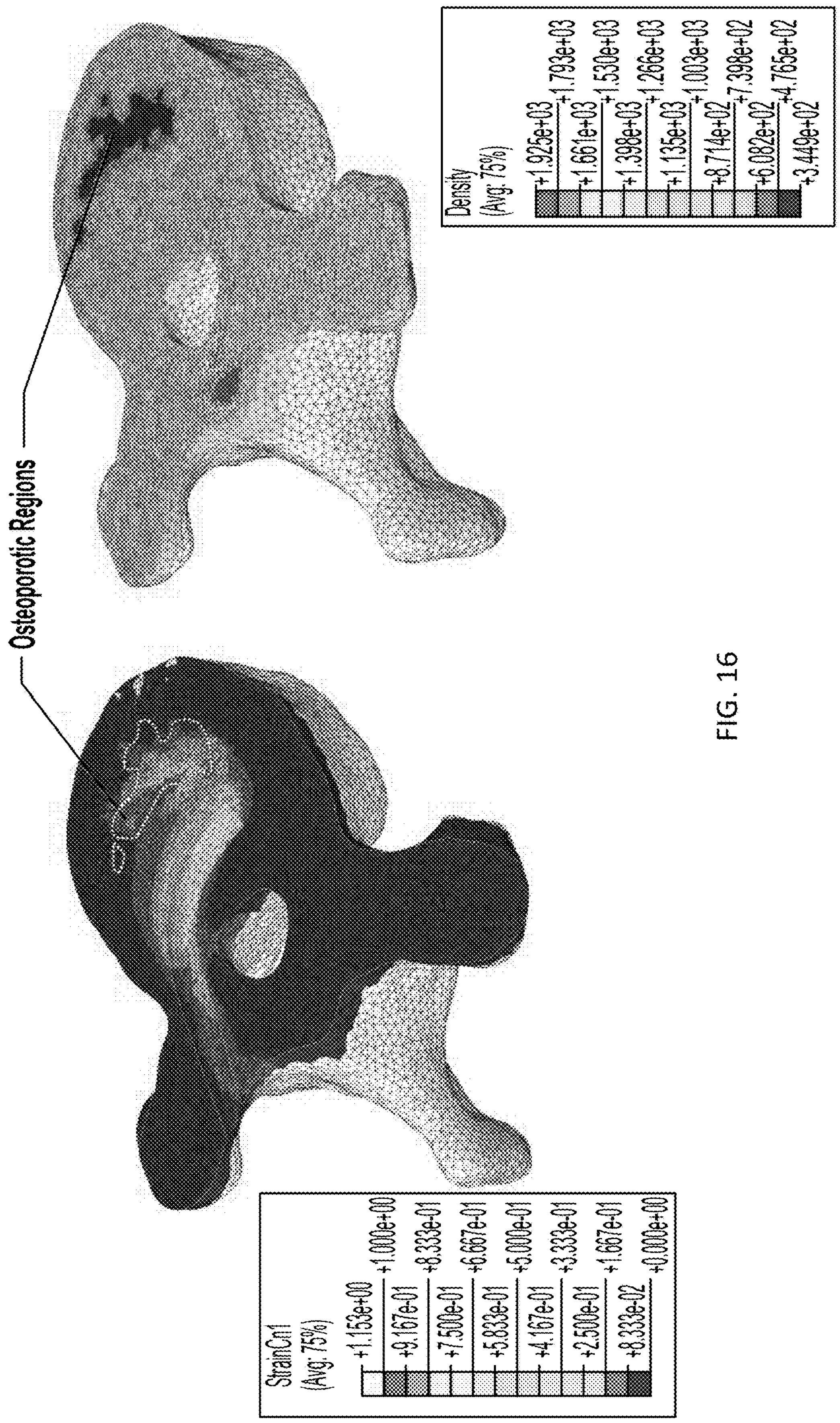

FIG. 16 depicts a schematic of stress distribution analysis of a curved implant path in a vertebra that avoids an osteoporotic region.

Figure 17:
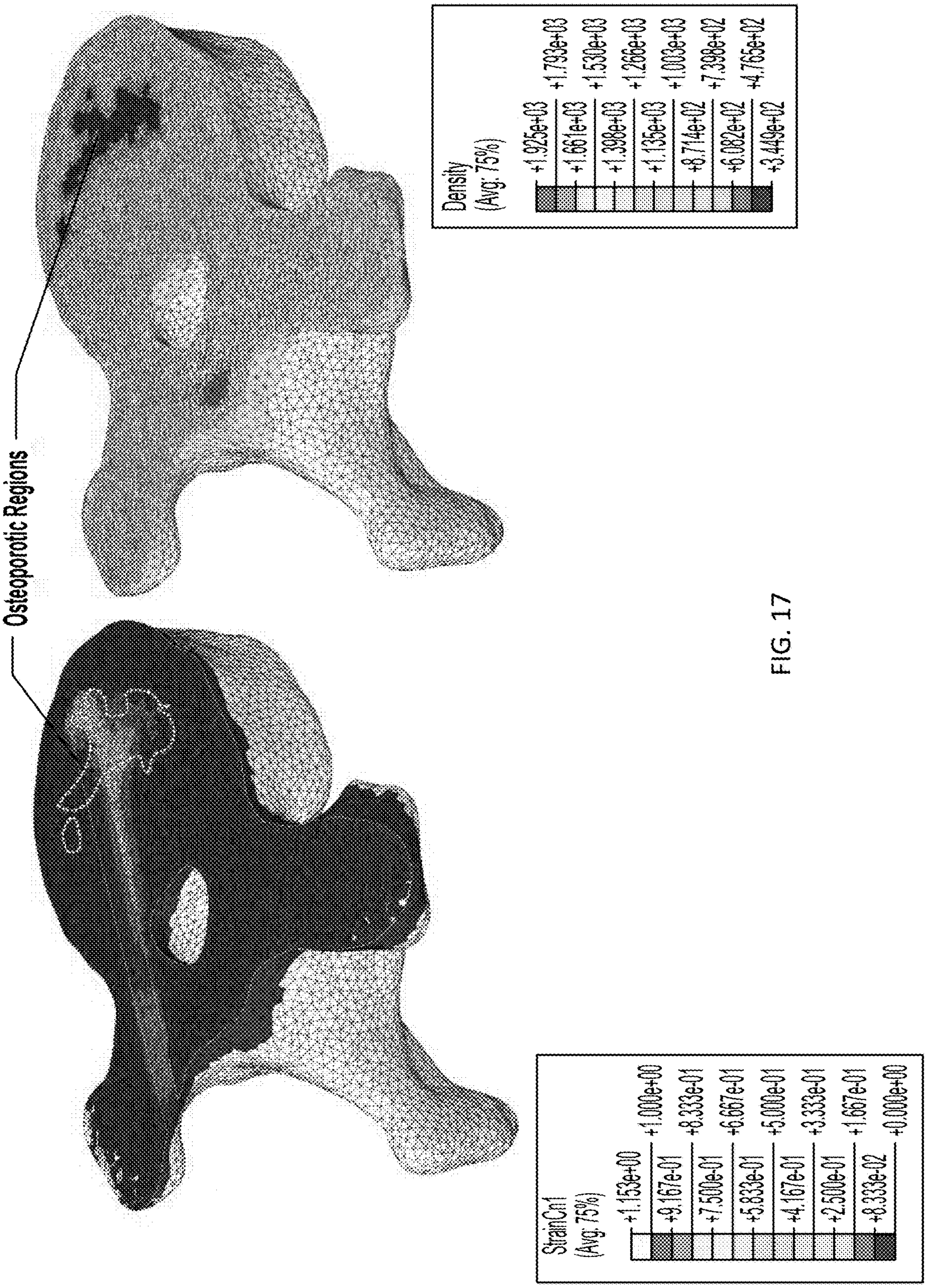

FIG. 17 depicts a schematic of stress distribution analysis of a straight implant path in a vertebra that passes through an osteoporotic region.

Figure 18:
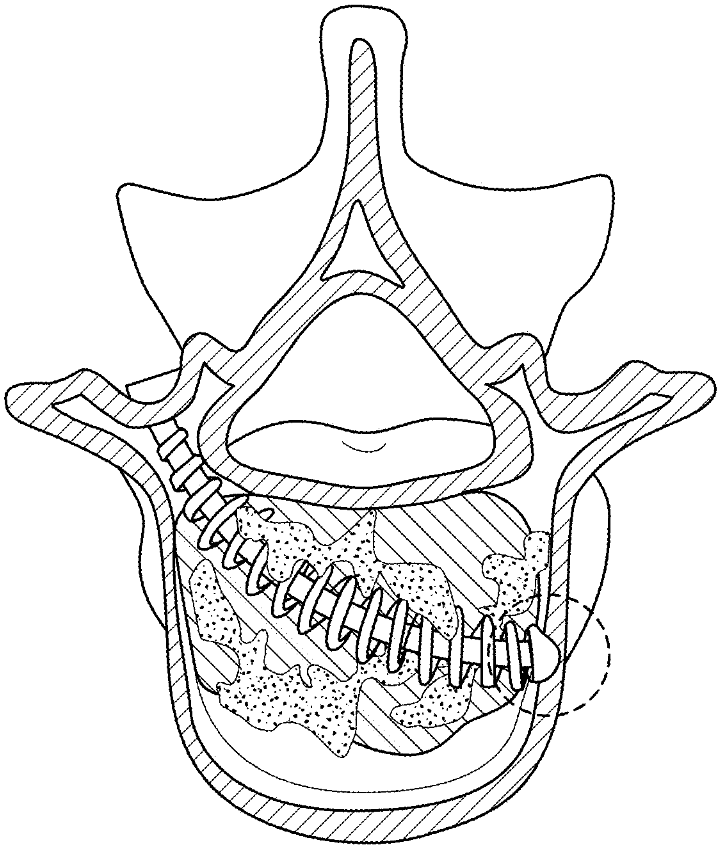

FIG. 18 depicts a diagram of a flexible implant fixed in bone such that a tip of the implant is driven into cortical bone.

Figure 19A:
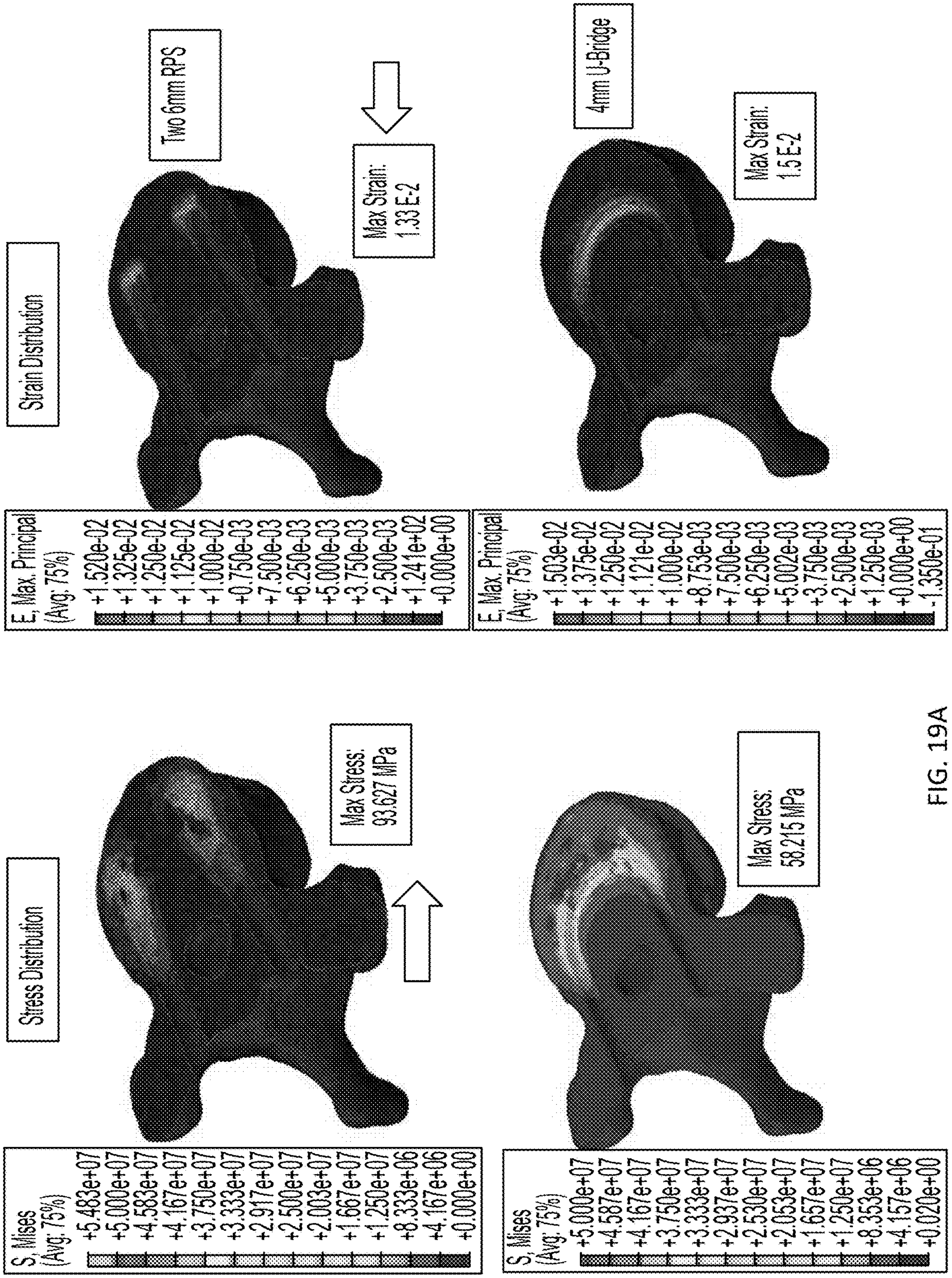

FIG. 19A depicts the results of finite element analysis with quantitative CT scan of an osteoporotic patient, comparing the performance of a traditional 6 mm rigid pedicle screw with a 4 mm U-bridge implant device.

Figure 19B:
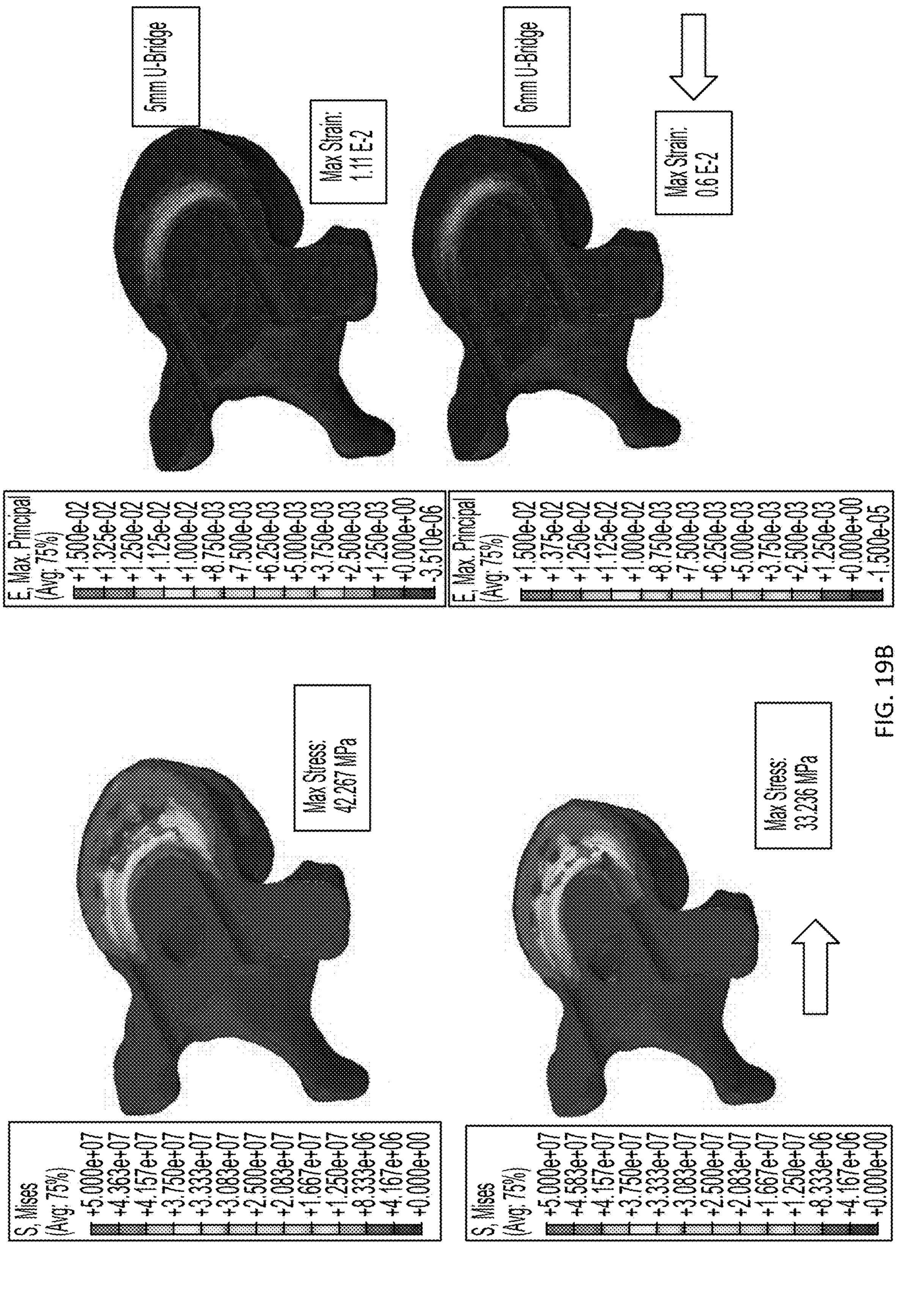
Figure 20A:
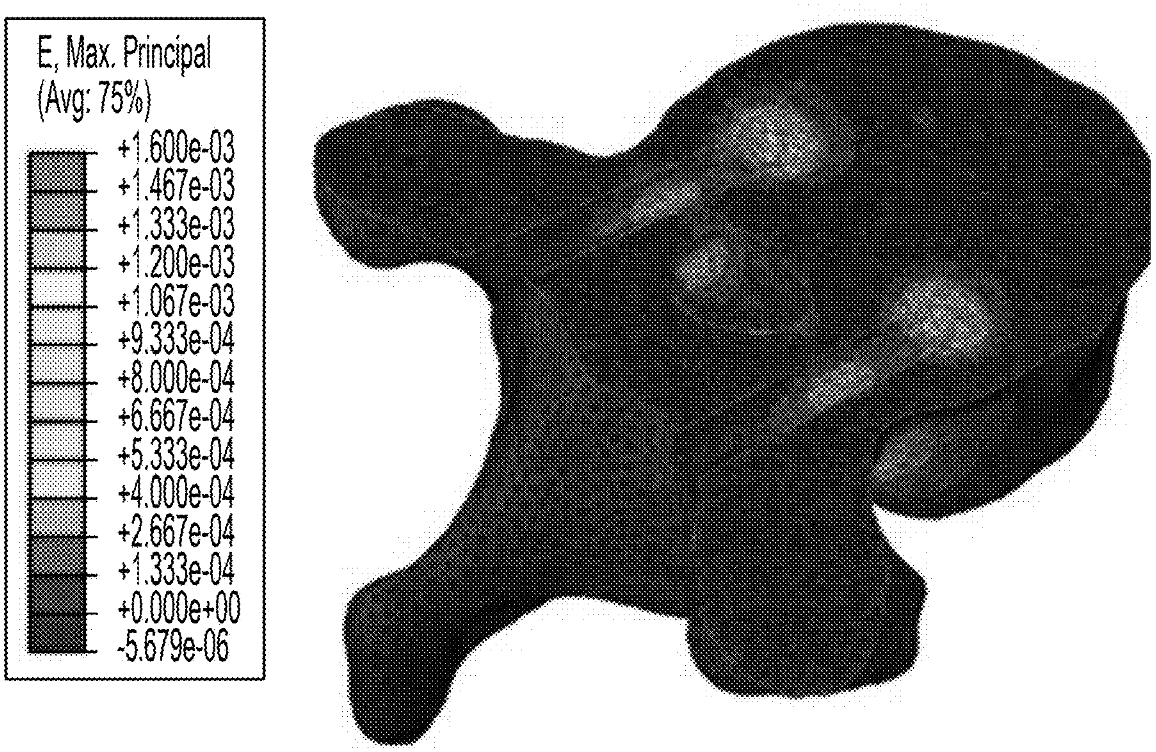
Figure 20B:
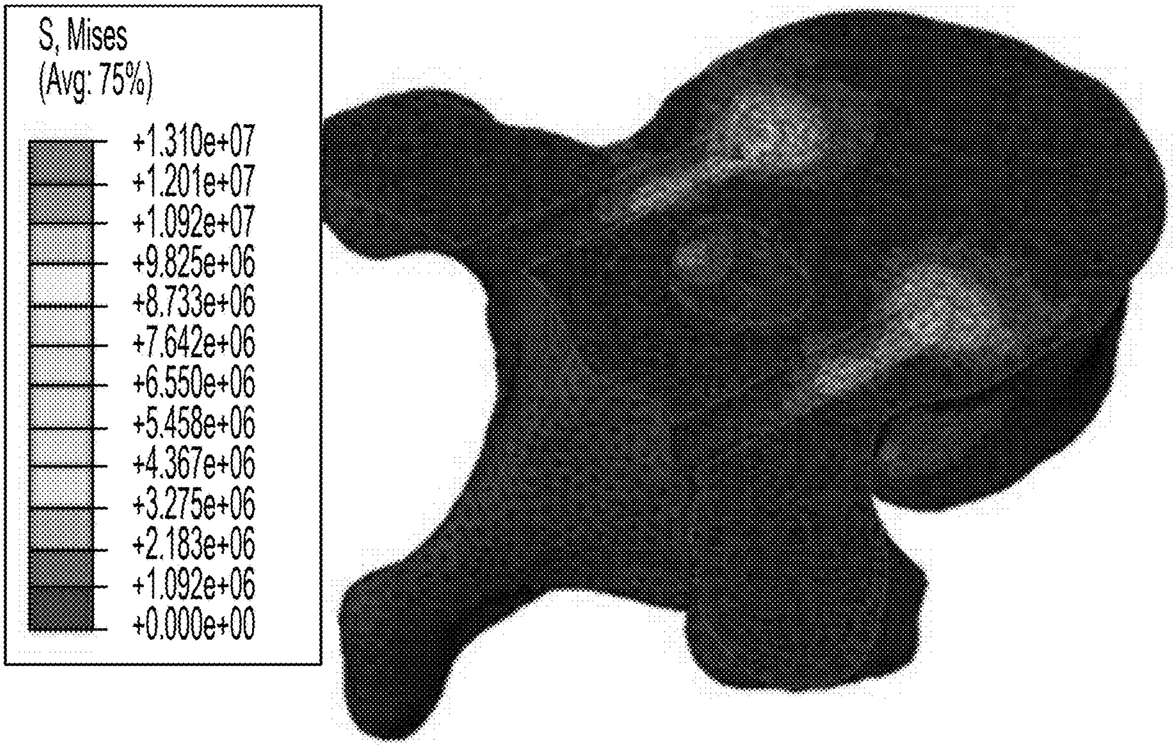
Figure 20C:
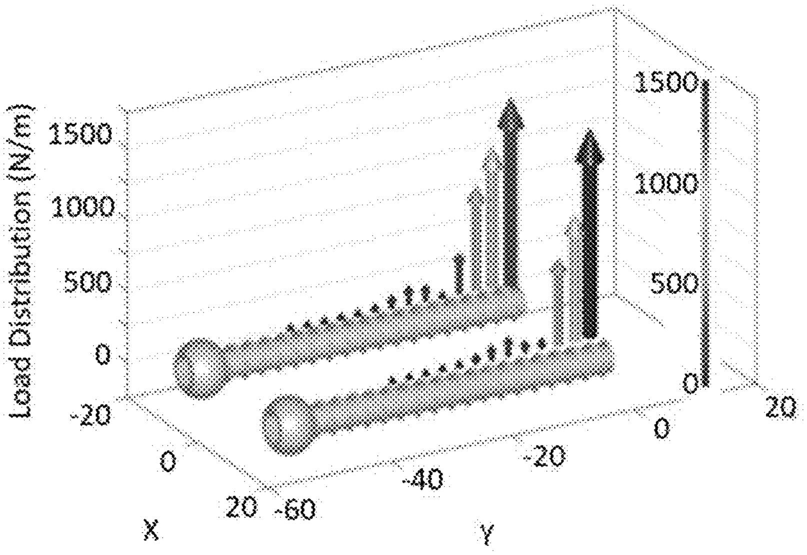
Figure 20D:
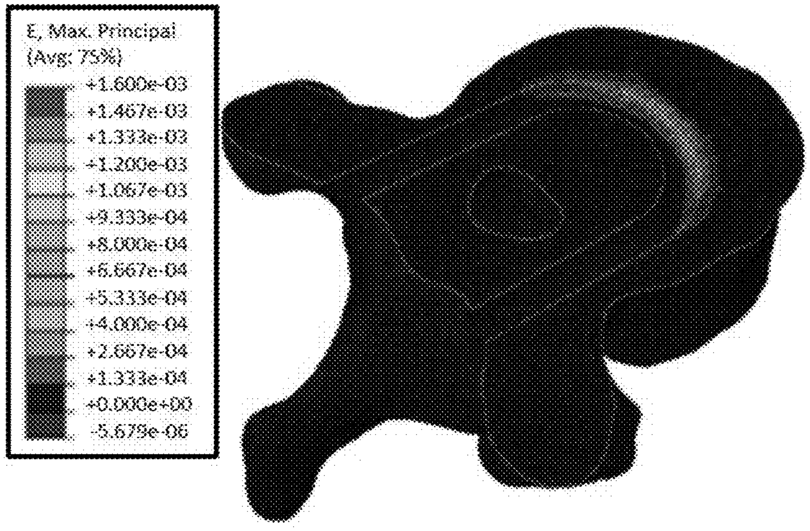
Figure 20E:
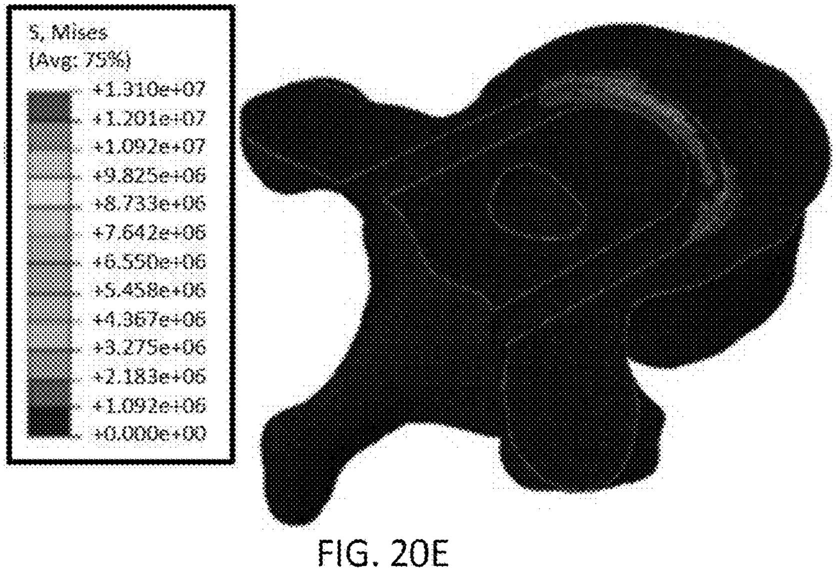
Figure 20F:
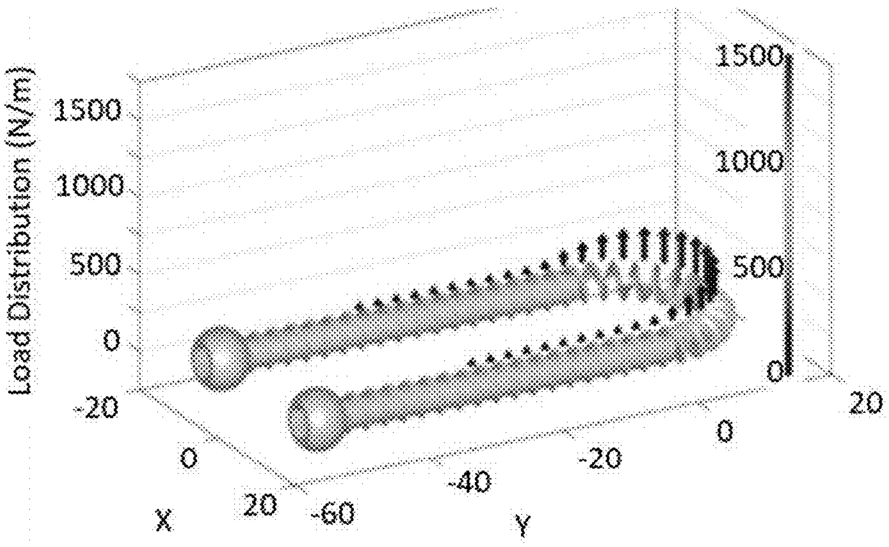

FIG. 19B depicts the results of finite element analysis with quantitative CT scan of an osteoporotic patient, comparing the performance of a 5 mm U-bridge implant device and a 6 mm U-bridge implant device. It should be noted that for 5 mm outer diameter implants, the U-bridge implant device reduces max stress by a factor of at least three and reduces max strain by a factor of at least two.

FIG. 20A through 20F depict the results of preliminary finite element analysis comparing the fixation performance of a conventional pedicle screw versus a U-bridge implant device performed on a quantitative CT scan of a patient with osteoporotic vertebra and under identical standing load conditions. (FIG. 20A) Pedicle screw stress distribution. (FIG. 20B) Pedicle screw strain distribution. (FIG. 20C) Load intensity distribution on pedicle screws. (FIG. 20D) U-bridge stress distribution. (FIG. 20E) U-bridge strain distribution. (FIG. 20F) Load intensity distribution on the U-bridge.

Figure 21A:
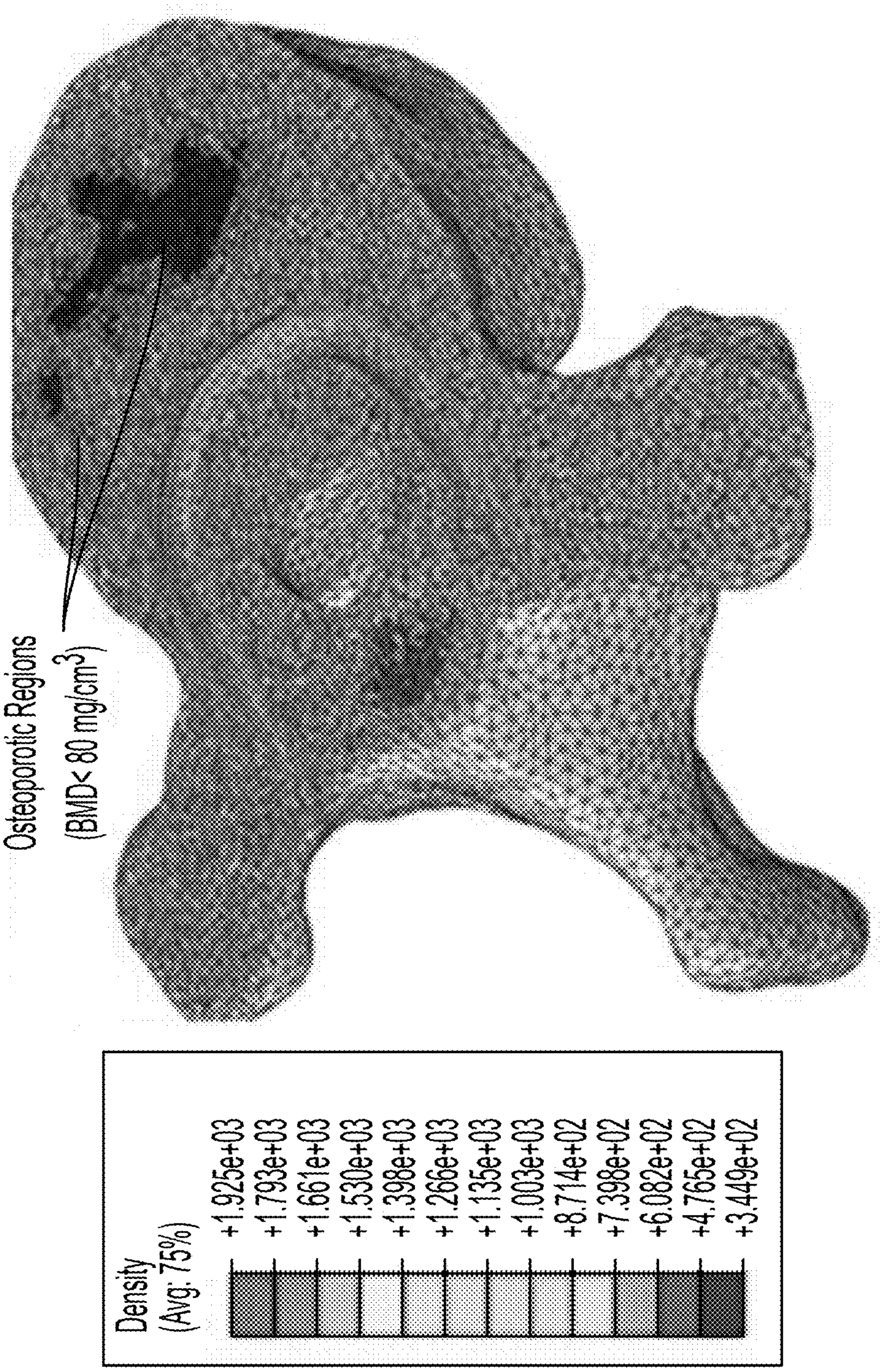
Figure 21B:
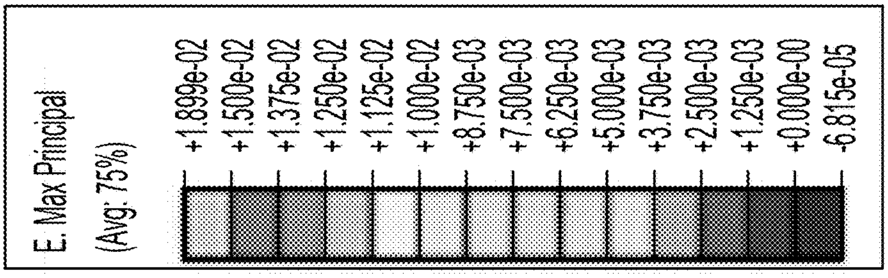
Figure 21B:
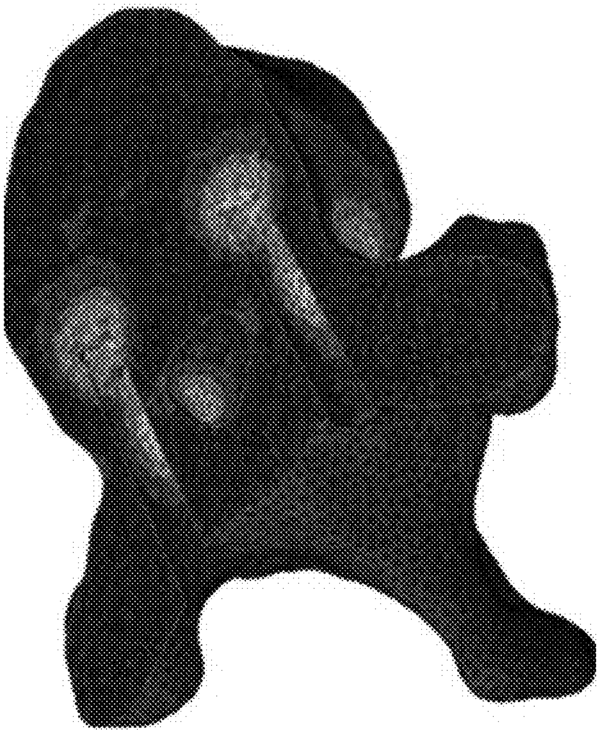
Figure 21C:
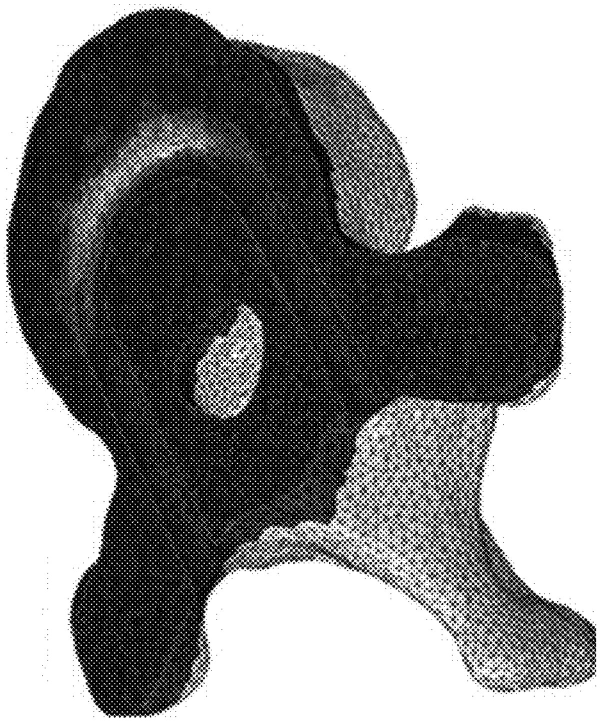

FIG. 21A through FIG. 21C depict the results of preliminary finite element analysis comparing the failure analysis of a conventional pedicle screw versus a U-bridge implant device under identical conditions. (FIG. 21A) Bone mineral density distribution. (FIG. 21B) Pedicle screw strain distribution). (FIG. 21C) U-bridge strain distribution.

Figure 22B:
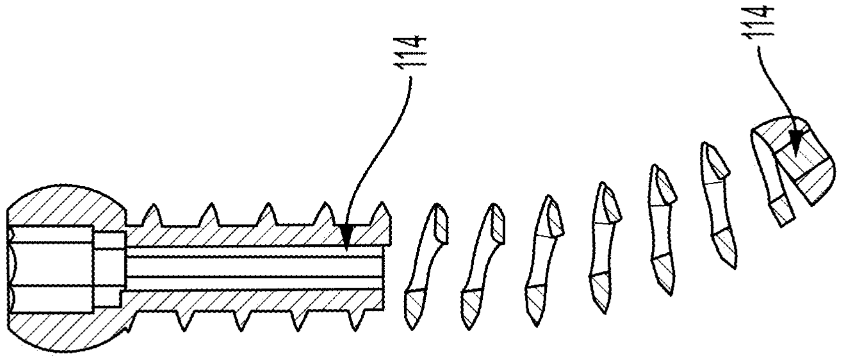
Figure 22A:
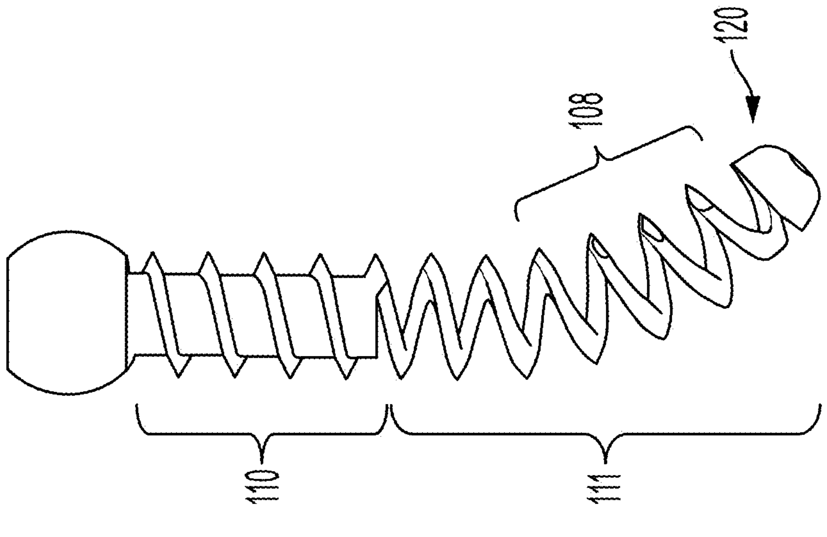

FIG. 22A through FIG. 22B depict conceptual designs of an exemplary flexible implant device illustrating the different design features of the screw including a rounded head of the screw, self-tapping threads of the screw, with flexible and rigid parts of the screw and a cannulated region of the screw. FIG. 22A illustrates the side view of the full flexible implant device screw and FIG. 22B shows the cross-section of the flexible implant device.

FIG. 23A through FIG. 23F depict experimental simulations of the tapping and bending capabilities of an exemplary flexible implant device. Both stress and deformation conditions are illustrated for three simulation conditions. FIGS. 23A-D represent stress and deformation for the flexible implant device under torsion conditions.

Figure 23A:
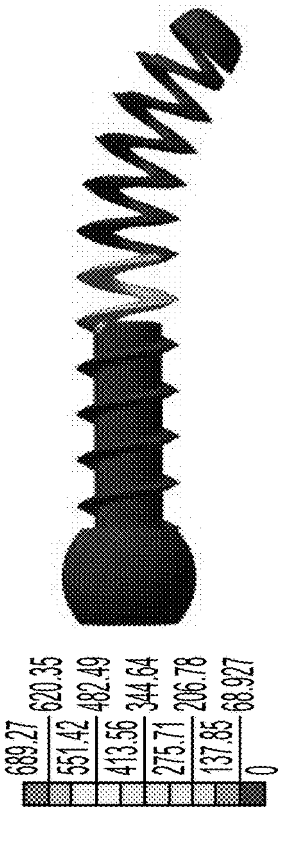
Figure 23B:
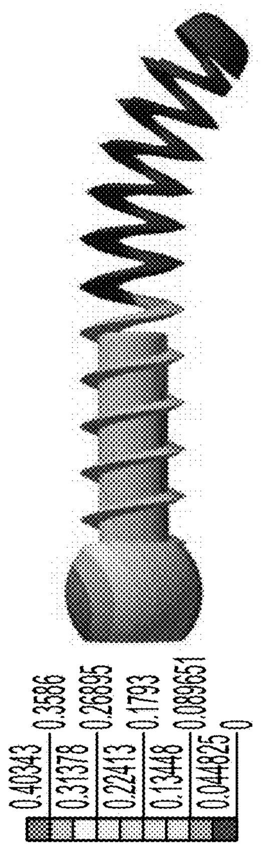

FIGS. 23A-B represent the torsion condition when all but the last two threads are inserted inside the vertebra while FIG. 23 C-D represent the torsion condition when only the first two threads are inserted inside the vertebra. FIGS. 23E-F represent stress and deformation for the flexible implant device under bending conditions.

Figure 24:
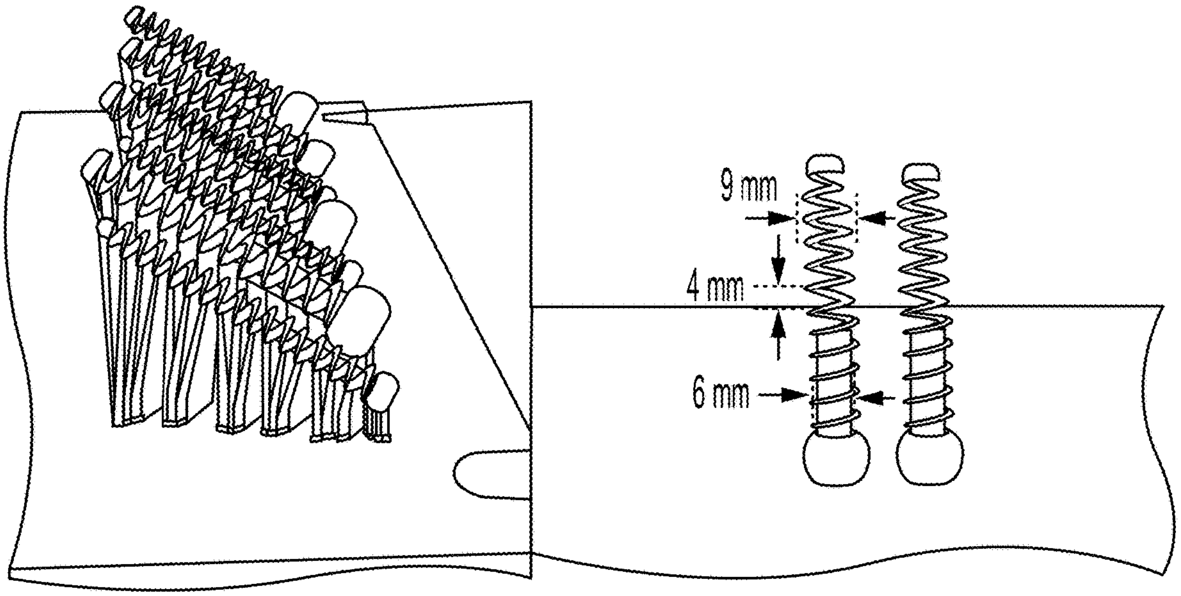

FIG. 24 shows images of metal 3D printed flexible pedicle screws. Two different sized flexible pedicle screws were fabricated on the build plate before post-processing (left). The first screw being a smaller 6 mm OD-4 mm ID version while the adjacent being the 9 mm OD-6 mm ID version with a V-shape screw thread utilized for the study. The 9 mm OD-6 mm ID screw after post-processing had been done including sandblasting (right).

Figure 25:
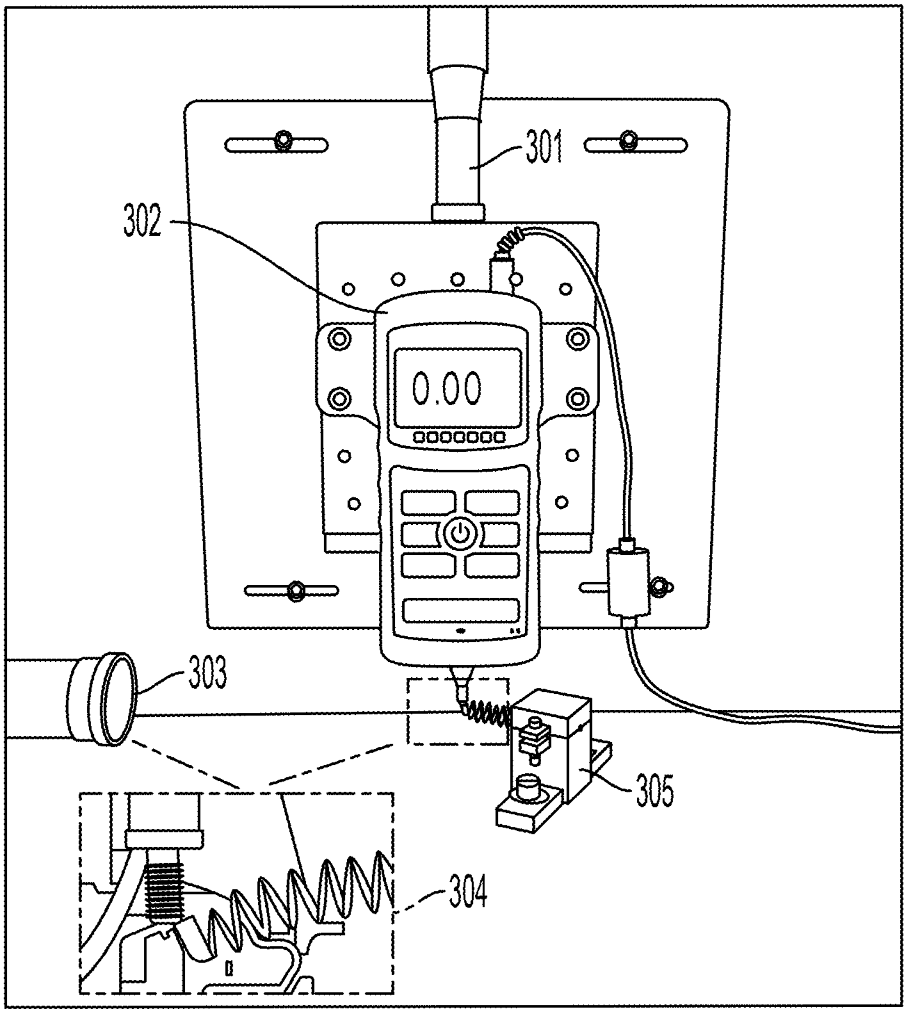

FIG. 25 illustrates the experimental set-up utilized to conduct force-displacement testing including the single-row linear stage 301, the digital force gauge 302, the side-view camera 303, the tip of force gauge touching screw tip as seen by side-view camera 304, and the testing fixture holding screw in place 305.

Figure 26A:
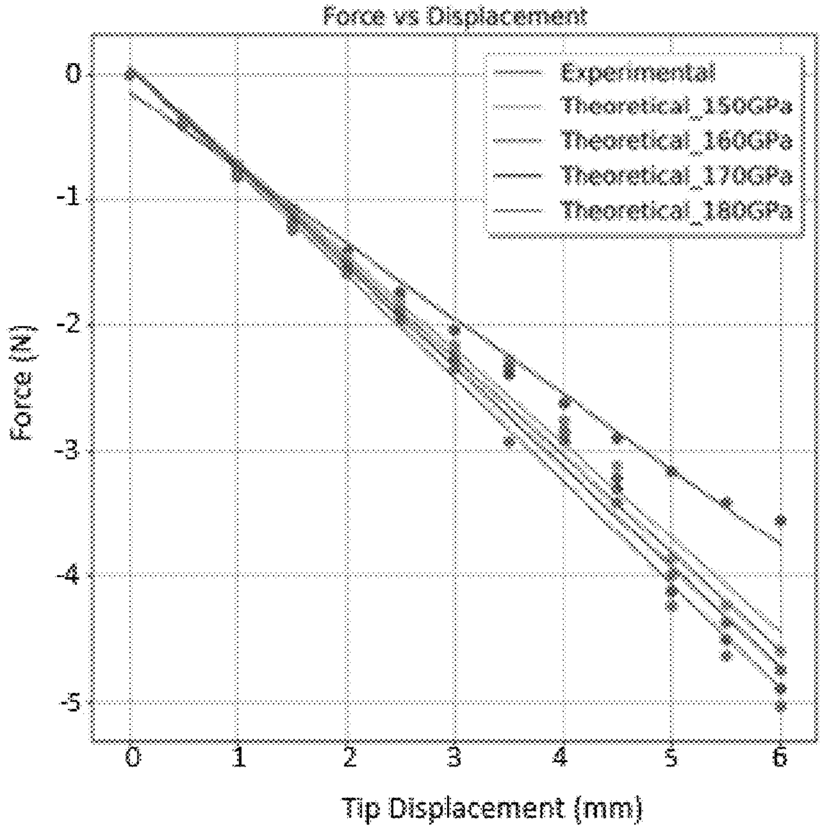
Figure 26B:
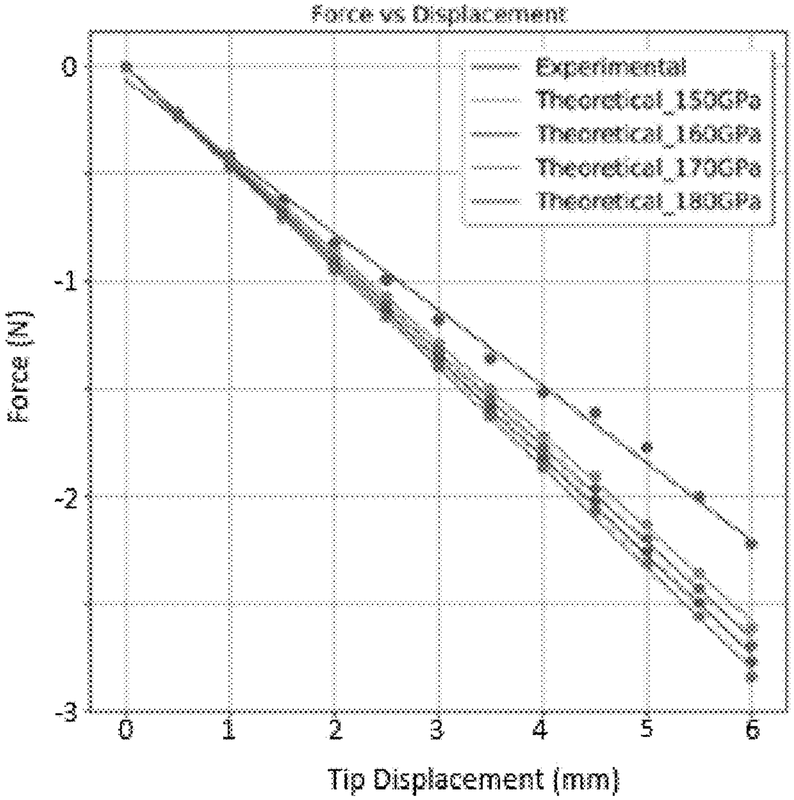
Figure 27A:
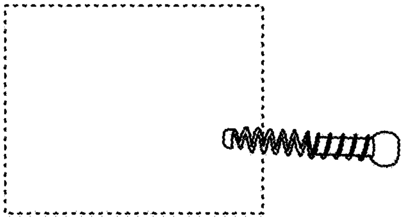
Figure 27B:
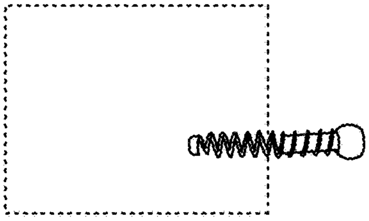
Figure 27C:
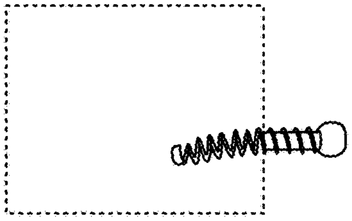
Figure 27D:
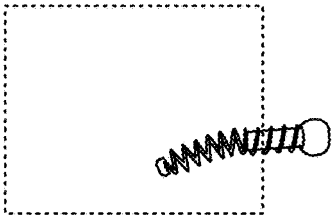
Figure 27E:
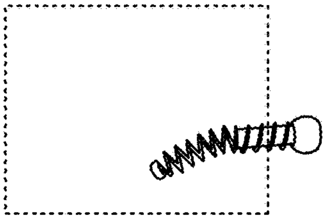
Figure 27F:
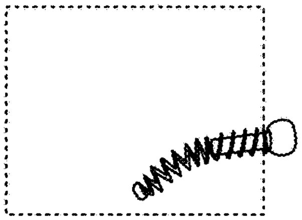

FIG. 26A through FIG. 26B shows plots of experimental results. FIG. 26A shows experimental force-displacement results achieved for a 9 mm screw during experimentation overlaid upon different theoretical Young's Modulus simulated to illustrate simulation efficacy to experiment. FIG. 26B shows experimental force-displacement results achieved for a 6 mm screw during experimentation overlaid upon different theoretical Young's Modulus simulated to illustrate simulation efficacy to experiment.

FIG. 27A through FIG. 27F show an experimental 9 mm OD-6 mm ID screw fully inserted inside a Sawbone to model how the screw would deform inside the vertebra. The screw is following a 35.7 mm radius of curvature created by the SDR, and is able to deform to approximately a 30.8 degree angle. The screw's self-tapping capability was used for proper internal fixation to occur.

Figure 28A:
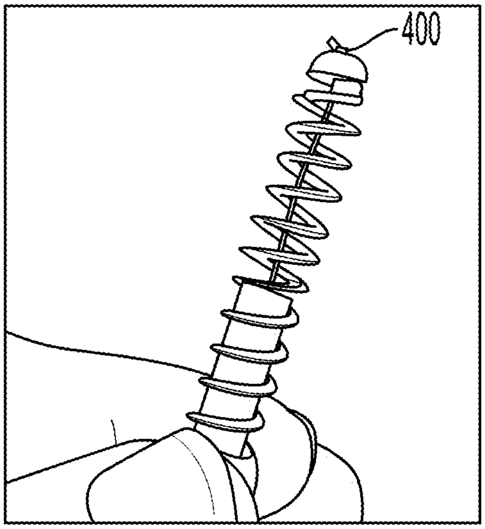
Figure 28B:
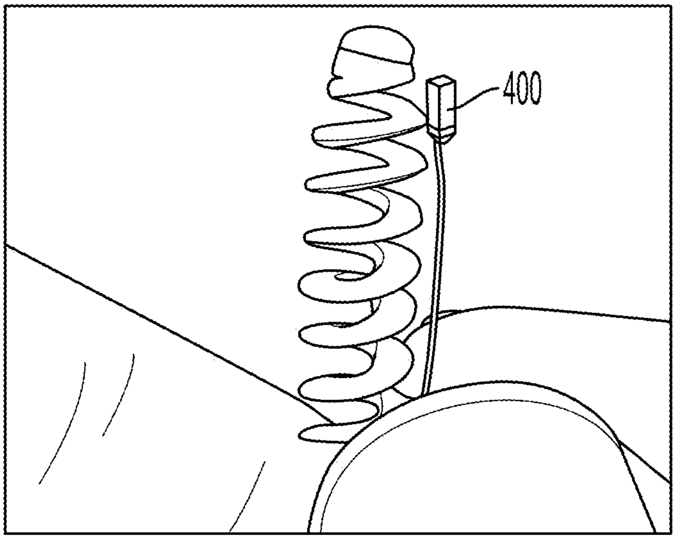
Figure 28C:
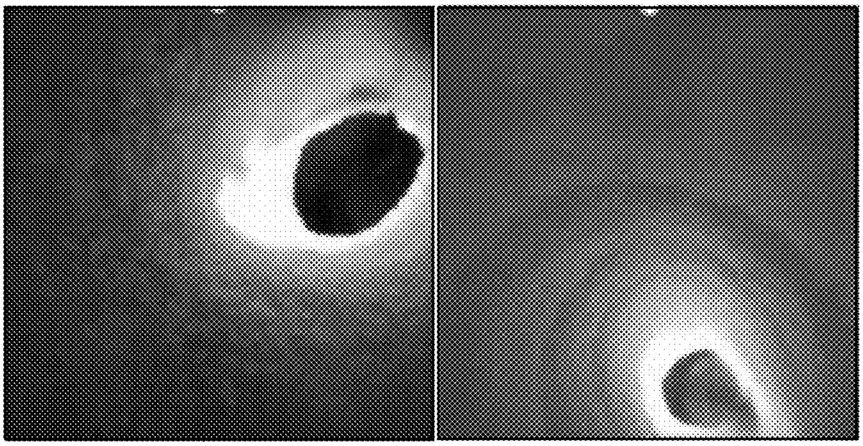

FIG. 28A through FIG. 28C show an experimental screw with an embedded camera 400. FIG. 28A shows an experimental screw with a camera 400 embedded within the tip. FIG. 28B shows a size comparison of the camera 400 to the experimental screw. FIG. 28C shows images from the camera during tapping and insertion of the experimental screw.

DETAILED DESCRIPTION

The present invention provides methods of forming flexible implant devices and U-Bridge implant devices that drive into the curved trajectories to enhance implant fixation in bone. The curved drilling trajectories avoid regions of low bone mineral density, such that implants driven into the curved drilling trajectories are anchored in regions of high bone mineral density to improve the stability of bone fixation. The implants are suitable for several applications, including but not limited to spinal fixation, orthopedic bone fixation, and neurosurgery.

Definitions

It is to be understood that the figures and descriptions of the present invention have been simplified to illustrate elements that are relevant for a clear understanding of the present invention, while eliminating, for the purpose of clarity, many other elements typically found in the art. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of +20%, +10%, +5%, +1%, and +0.1% from the specified value, as such variations are appropriate.

The terms "proximal," "distal," "anterior," "posterior," "medial," "lateral," "superior," and "inferior" are defined by their standard usage indicating a directional term of reference. For example, "proximal" refers to an upper location from a point of reference, while "distal" refers to a lower location from a point of reference. In another example, "anterior" refers to the front of a body or structure, while "posterior" refers to the rear of a body or structure. In another example, "medial" refers to the direction towards the midline of a body or structure, and "lateral" refers to the direction away from the midline of a body or structure. In some examples, "lateral" or "laterally" may refer to any sideways direction. In another example, "superior" refers to the top of a body or structure, while "inferior" refers to the bottom of a body or structure. It should be understood, however, that the directional term of reference may be interpreted within the context of a specific body or structure, such that a directional term referring to a location in the context of the reference body or structure may remain consistent as the orientation of the body or structure changes.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments there between. This applies regardless of the breadth of the range.

Flexible Implant Device

Figure 1A:
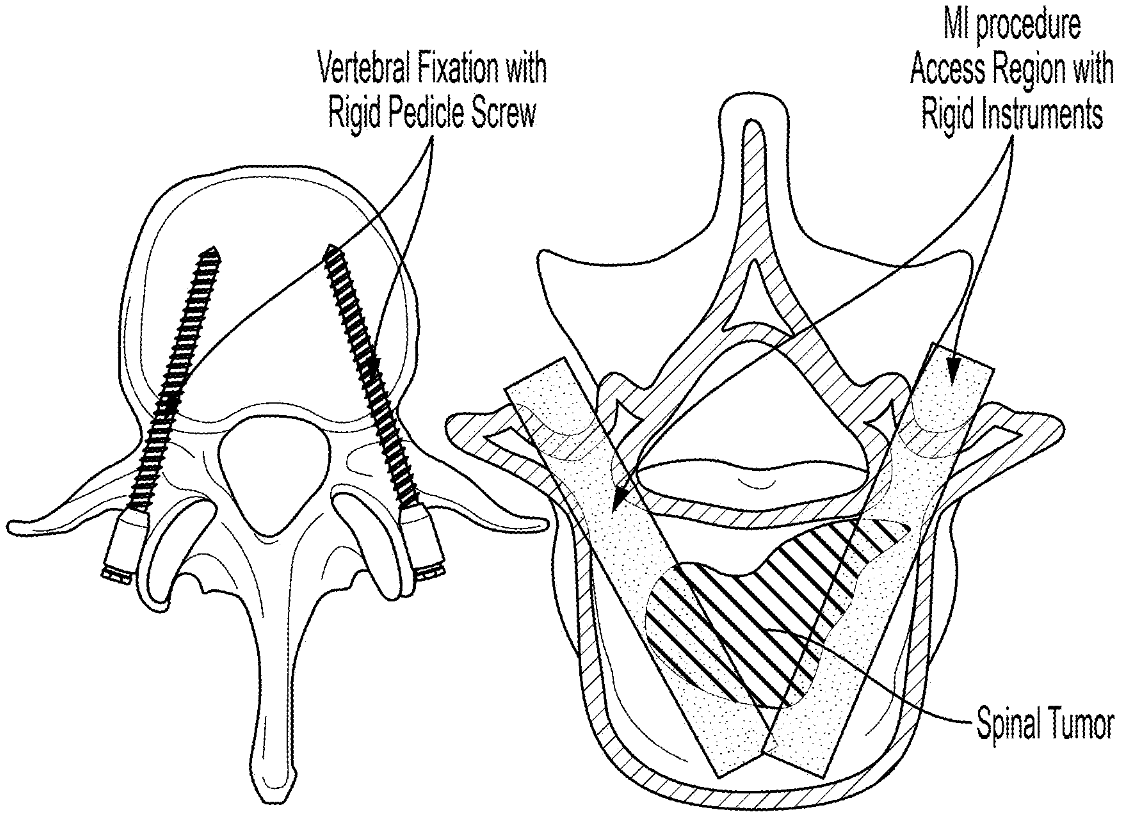
FIG. 1A through FIG. 1D depicts schematics of spinal fixation comparing the use of rigid, linear pedicle screws to exemplary flexible implant devices and U-bridge implant devices.
Figure 1B:
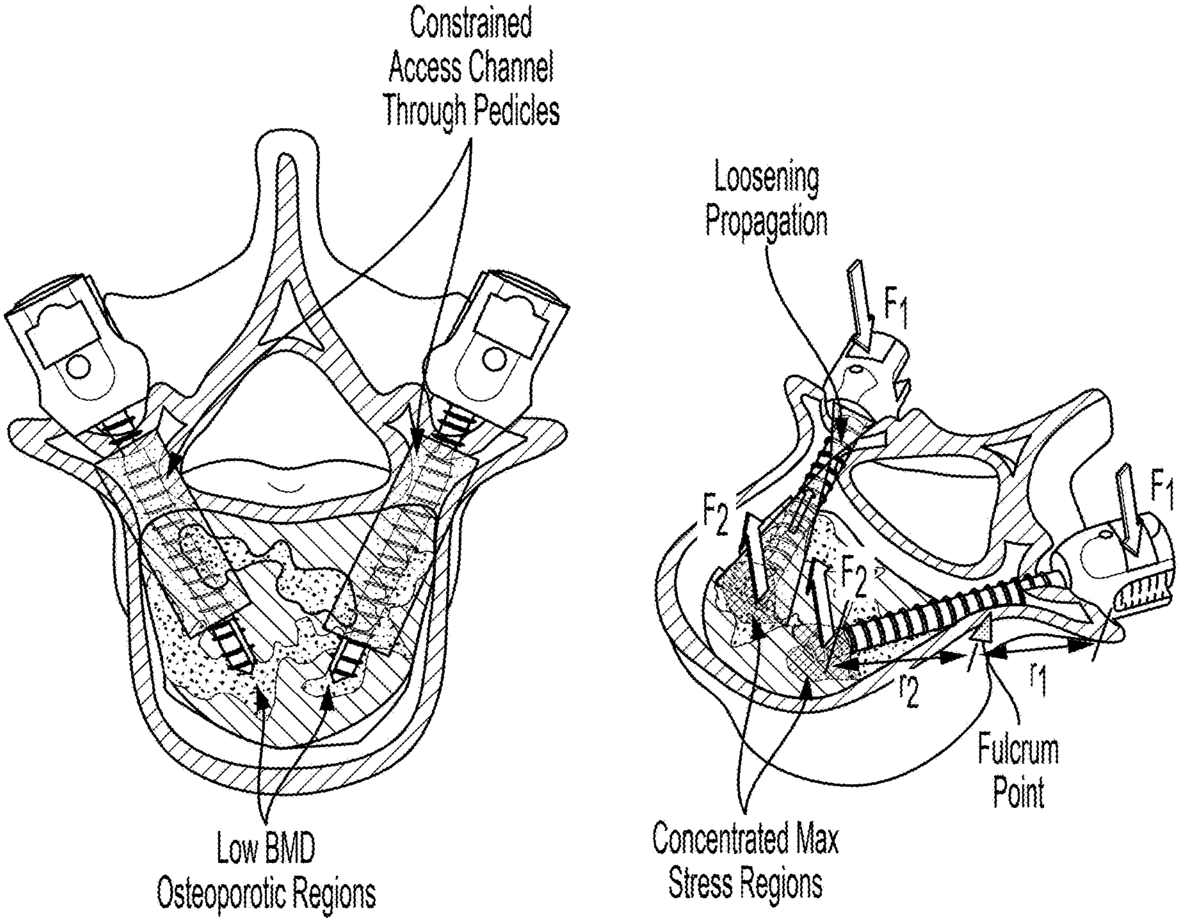
Figure 1C:
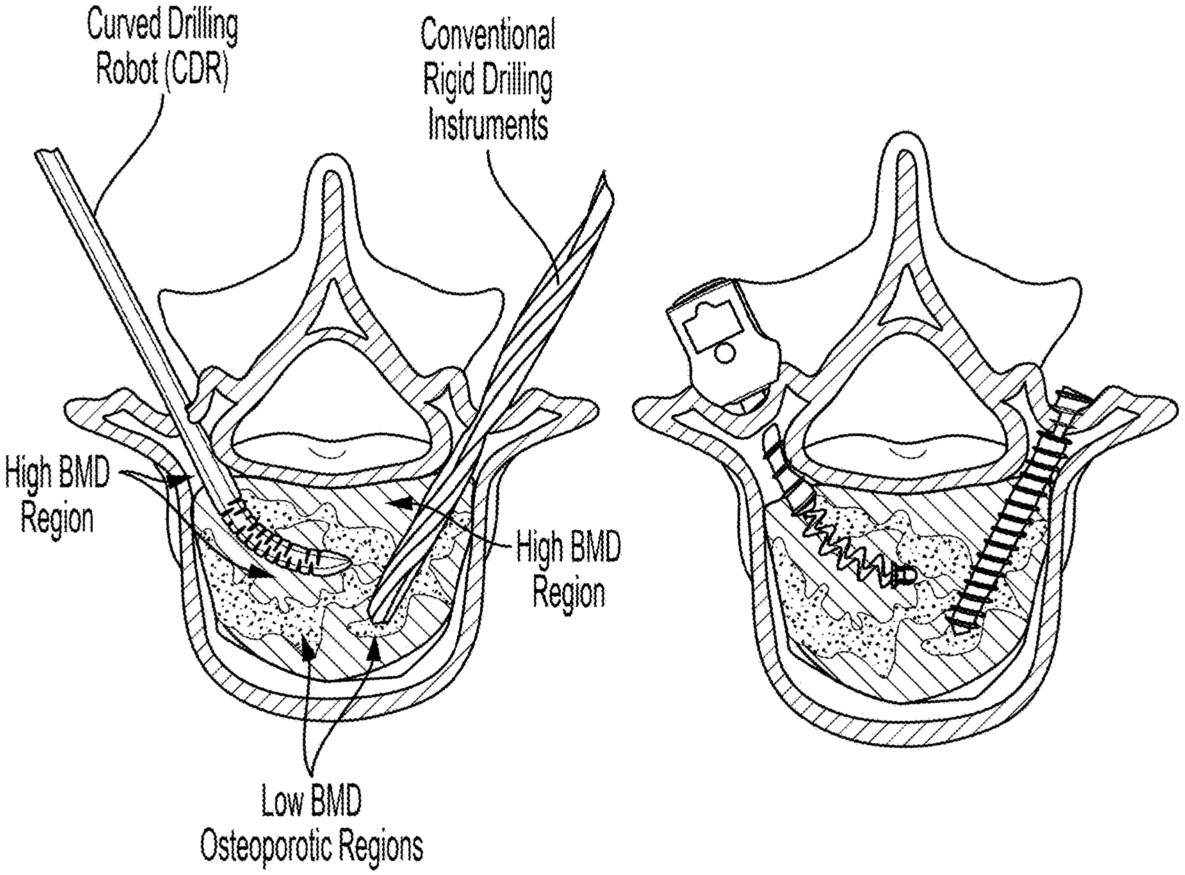
Figure 1D:
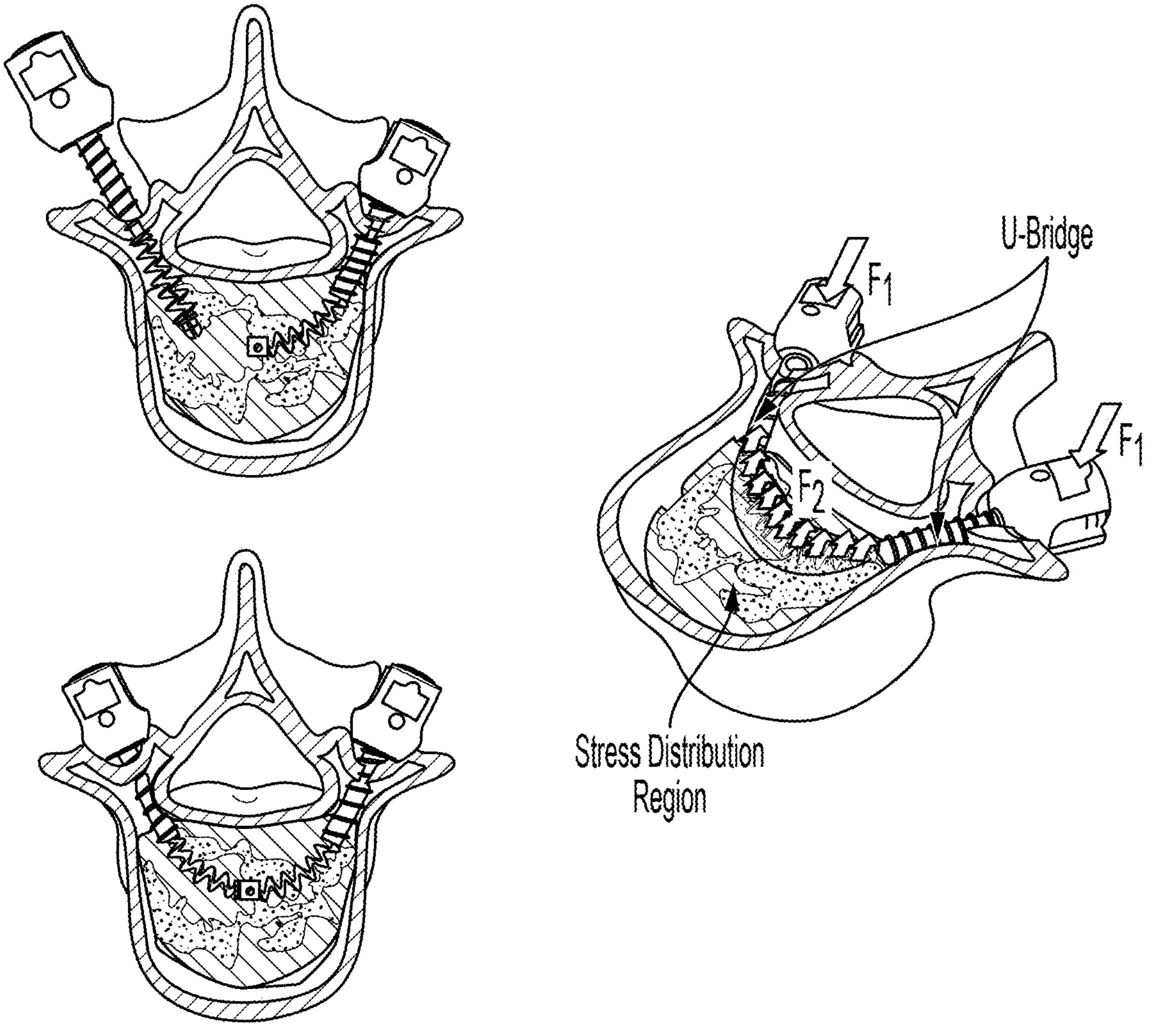
Figure 2:
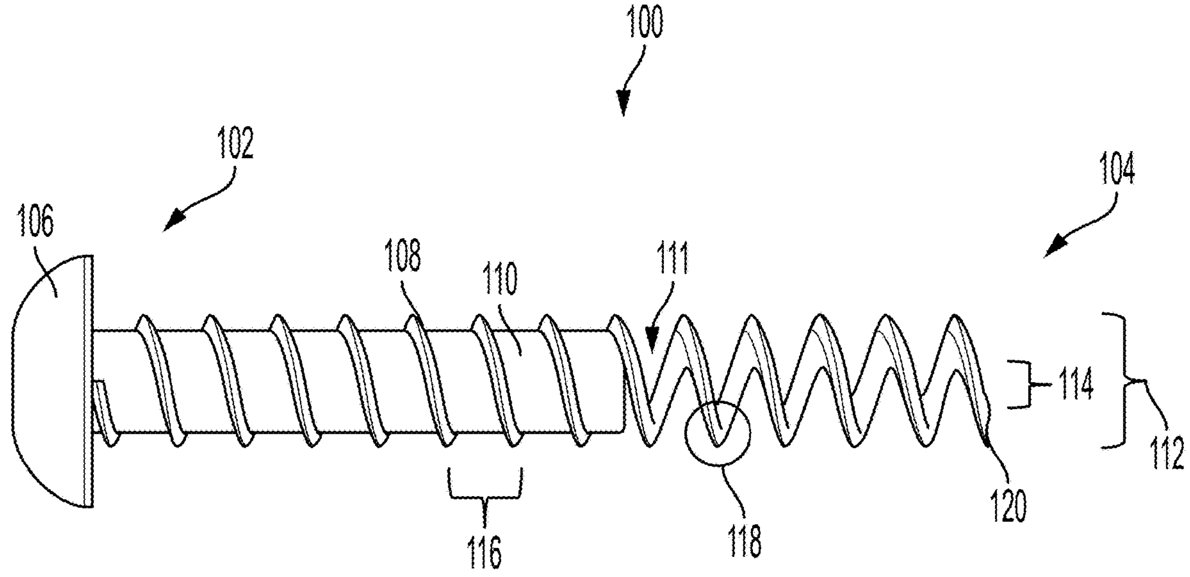
FIG. 2 depicts a side view of an exemplary flexible implant device.
Figure 3:
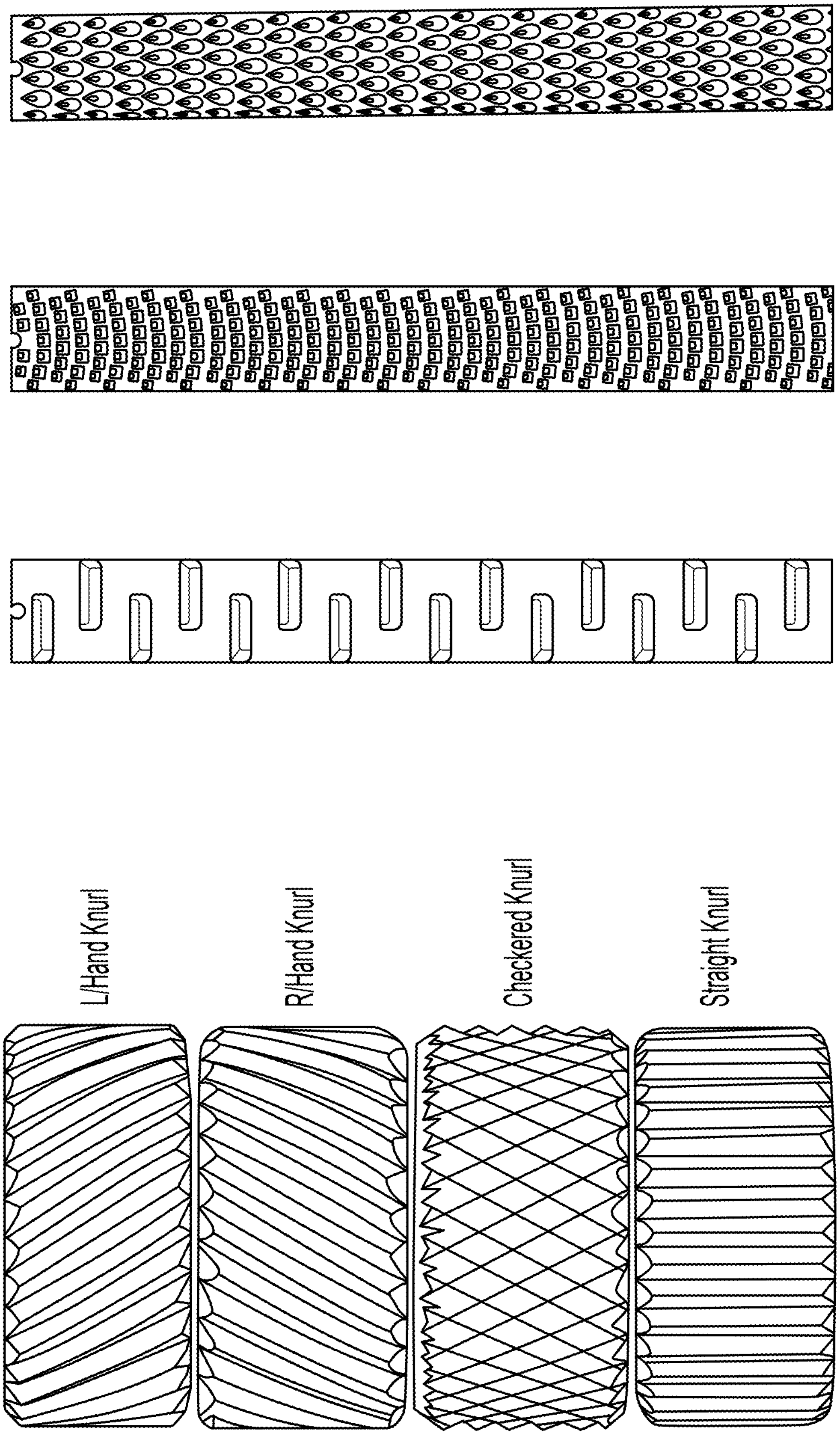
FIG. 3 depicts a schematic of exemplary engagement member surfaces, including knurled patterns (left) and grating patterns (right).

Referring now to FIG. 2, an exemplary flexible implant device 100 is depicted. Device 100 comprises a length extending between a proximal end 102 and a distal end 104. Device 100 comprises a screw head 106 at proximal end 102, a rigid shank 110 extending towards distal end 104 for a portion of the length, and a flexible engagement member 108 extending from shank 110 to a tip 120 at distal end 104. Tip 120 can be any suitable tip, such as a self-tapping tip, a blunt tip, and a sharp tip. Engagement member 108 forms a spiral, helical, or spring-like shape and is at least partially formed around a shank-less space 111. Engagement member 108 comprises an outer facing surface configured to grip onto an implant site, wherein the outer facing surface comprises an engagement structure including but not limited to a screw thread (FIG. 2), a knurling pattern (FIG. 3, left), a grating pattern (FIG. 3, right), and combinations thereof. In some embodiments, engagement member 108 extends for at least a portion over a length of shank 110. In some embodiments, engagement member 108 extends for the entire length of shank 110 and reaches screw head 106. Accordingly, device 100 comprises at least one rigid portion corresponding to a length of shank 110 and at least one flexible portion corresponding to a length of engagement member 108 that is free from shank 110.

Engagement member 108 has an outer diameter 112, an inner diameter 114, and a cross-sectional shape 118. Outer diameter 112 can be any suitable size, such as in a range between about 1 and 10 mm, as well as a variable size along the length of device 100 between about 1 and 10 mm. In some embodiments, engagement member 108 comprises a constant outer diameter 112, such that device 100 comprises a substantially cylindrical shape. In some embodiments, engagement member 108 comprises a variable outer diameter 112, such that device 100 comprises a substantially conical shape wherein a proximal outer diameter 112 is wider than a distal outer diameter 112. In various embodiments, device 100 comprises a combination of sections having a constant outer diameter 112 and sections having a variable outer diameter 112. Inner diameter 114 can be any suitable size, such as in a range between about 0 and 9 mm, as well as a variable size along the length of device 100 between about 0 and 9 mm. In some embodiments wherein engagement member 108 is a screw thread, engagement member 108 can further comprise a thread pitch 116. Thread pitch 116 is a measure between adjacent threads, and can be any suitable size, such as in a range between about 0.1 and 5 mm, as well as a variable size along the length of device 100 between about 0.1 and 5 mm. While the exemplary device 100 is depicted in FIG. 2 as having a substantially triangular cross-sectional shape 118, it should be understood that device 100 can have any cross-sectional shape 118, including but not limited to square shapes, pentagon shapes, hexagon shapes, rectangular shapes, rhombus shapes, diamond shapes, trapezoid shapes, and the like. Cross-sectional shape 118, as well as the size of cross-sectional shape 118, can also be variable along the length of device 100. In some embodiments, the varying cross-sectional shapes described above are equally applicable to shaft 110 and inner diameter 114.

In some embodiments, the flexible implant devices are provided in a series of preset dimensions and shapes. In this manner, an appropriate flexible implant device may be selected at the time of use. In some embodiments, the flexible implant devices of the present invention are tailored in that the devices are fabricated with dimensions and shapes based on the characteristics of a subject and are specific to a subject. As described elsewhere herein, the implant devices comprise several components having dimensions and shapes that that may be selected from a range, including but not limited to shank length, engagement member length, screw thread pitch (where engagement member is a screw thread), engagement member outer diameter, engagement member inner diameter, engagement member cross-sectional shape, and tip. Characteristics of a subject that may determine the specific construction of a flexible implant device include but are not limited to: bone mineral density, bone mineral distribution, cortical bone thickness, cancellous bone thickness, type of insertion (such as insertion in cancellous bone and/or passing through cancellous bone and anchoring a distal end of a flexible implant device to cortical bone in a curved trajectory), curvature of a drilling trajectory, plane of insertion in to bone, and the like. An implant device specific to a subject may then be fabricated having a specific shank length, engagement member length, screw thread pitch, engagement member outer diameter, engagement member inner diameter, engagement member cross-sectional shape, and/or tip to form the curvatures necessary to conform to the characteristics of the subject. In some embodiments, the type of surgical application and access point to a bone may determine the geometry of a flexible implant device, including but not limited to its length, thread pitch, shank length, inner diameter, and outer diameter. For example, in the surgical application of a pelvic fracture, a flexible implant device may have a long length and a thin outer diameter geometry.

Figures 4A, 4B, 4C:
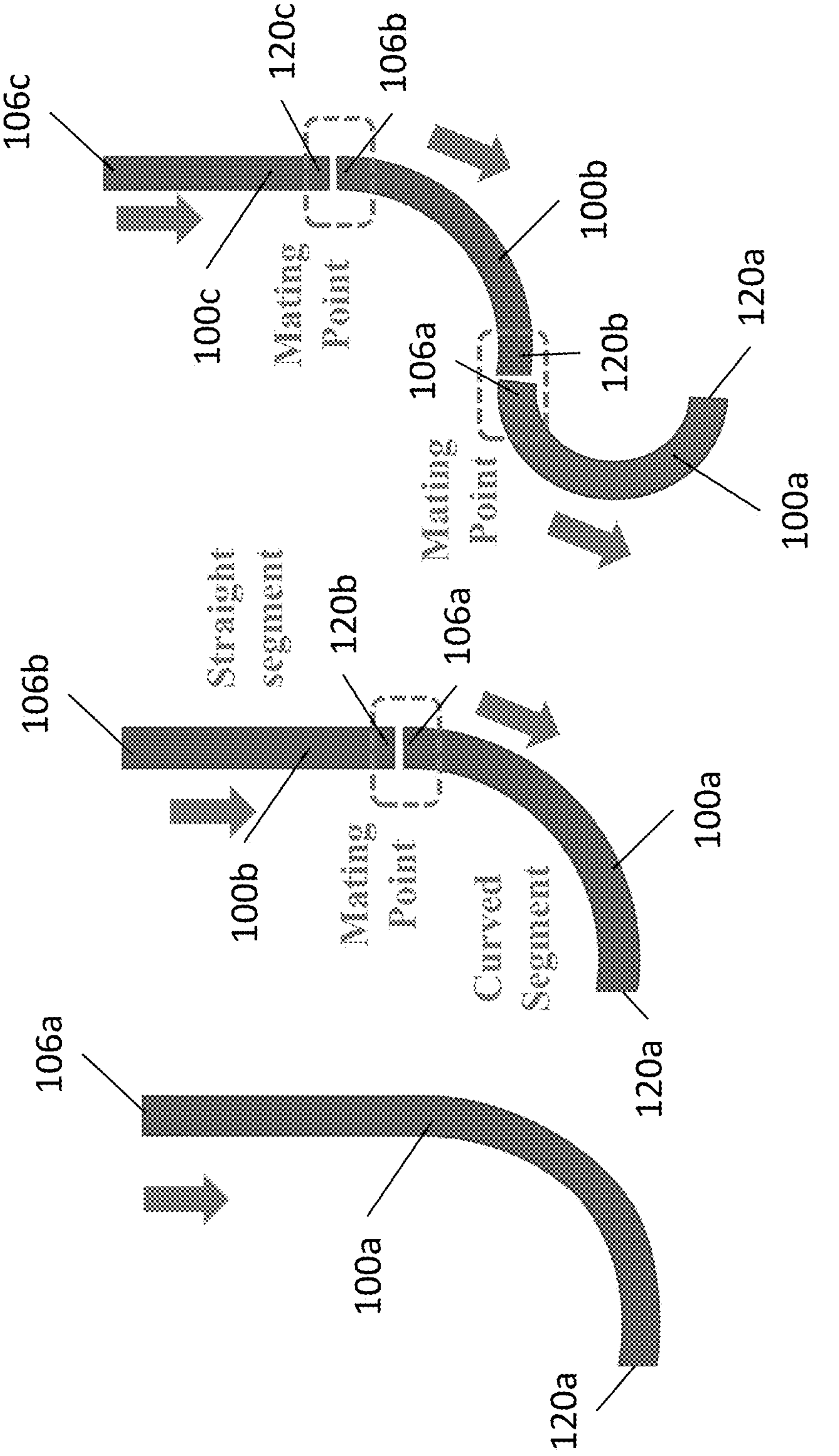
FIG. 4A through FIG. 4C depict diagrams of exemplary flexible implant devices of varying lengths. Flexible implant devices can be used as solitary implants (FIG. 4A) or joined together (FIG. 4B, FIG. 4C). The arrows show the direction of implant insertion.
Figure 5:
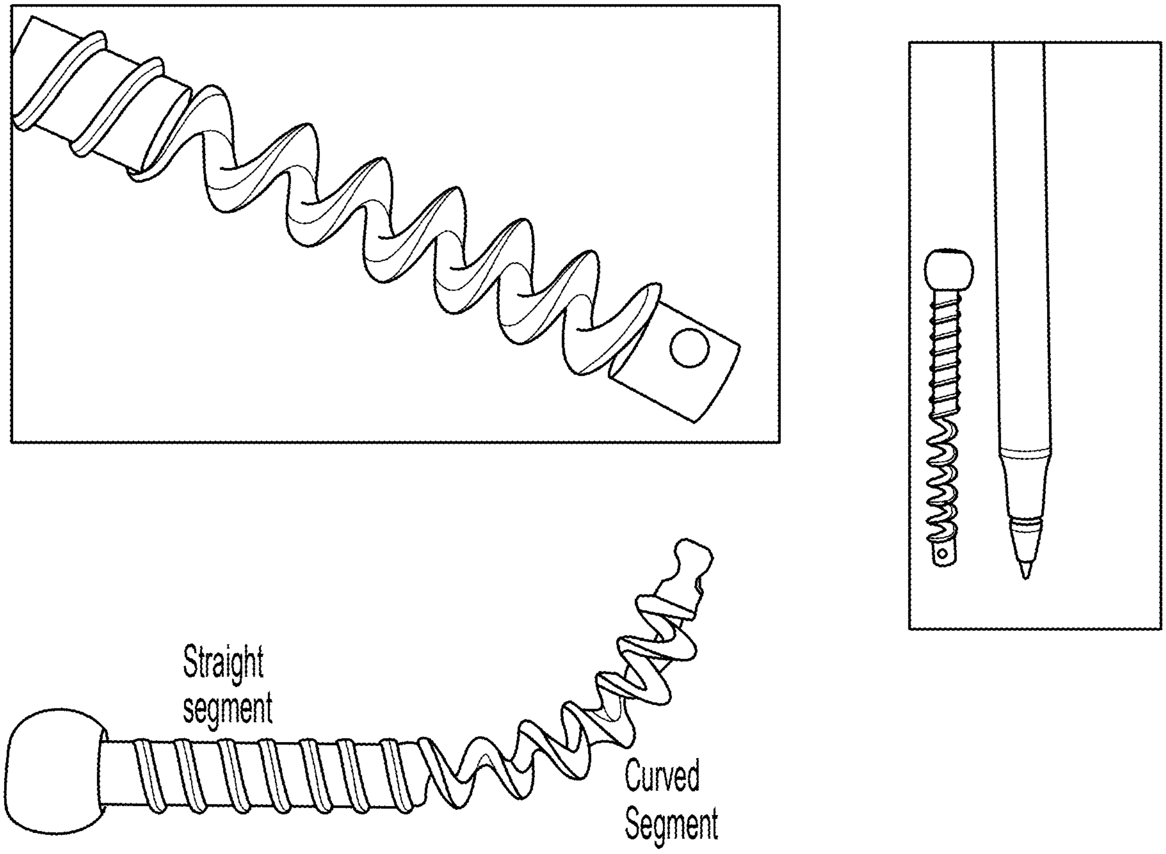
FIG. 5 depicts an exemplary flexible implant constructed from steel.

In some embodiments, device 100 can be mated to one or more additional devices 100. The joining of multiple devices 100 can form an overall general shape of an implant having a combination of straight and curved segments configured to conform to any arbitrary-shaped drilled hole. Each device 100 can comprise a tip 120 configured to mate to a screw head 106, wherein each device 100 can be used interchangeably to mate to additional devices 100. Tip 120 can thereby comprise a mating connection, including but not limited to a push lock fitting, a threaded connector, and a magnet. Referring now to FIG. 4A through FIG. 4C, device **100*a* is implanted as a single continuous implant (FIG. 4A). If desired, a second device 100*b* can be implanted end-to-end with device 100*a*, wherein tip 120*b* mates with and/or drives screw head 106*a*. If desired, a third device 100*c* can be implanted end-to-end with device 100*a* and device 100*b*, wherein tip 120*c* mates with and/or drives screw head 106*b*, which in turn may drive tip 120*b* and screw head 106*a*. It should be understood that any desired number of devices 100 may be used in combination, and each device 100** in a combination may comprise the same or different attributes as described elsewhere herein (shank length, engagement member length, screw thread pitch (where engagement member is a screw thread), engagement member outer diameter, engagement member inner diameter, engagement member cross-sectional shape, and the like).

While exemplary flexible implant devices of the present invention are described above, the flexible implant devices are nonetheless amenable to any suitable modification to augment their function. For example, in various embodiments, the flexible implant devices can include one or more surface coatings that are configured to enhance pullout strength, biocompatibility, or both. Contemplated coatings include but are not limited to PEEK, PTFE, hydroxyapatite, and the like. In some embodiments, the flexible implant devices can accept a bone cement. Sections of the implant devices that are shank-less can receive a bone cement injection within an inner diameter that can set after implantation to improve rigidity and pullout strength. In some embodiments, sections of the implant devices that include a shank can further comprise a lumen within the shank to facilitate the injection of a bone cement into the shank-less sections. In various embodiments, the implant devices can be further reinforced by the insertion of one or more wires into the shank-less sections.

The flexible implant devices of the present invention can be made using any suitable method known in the art. The method of making may vary depending on the materials used. For example, components substantially comprising a metal may be milled from a larger block of metal or may be cast from molten metal. Likewise, components substantially comprising a plastic or polymer may be milled from a larger block, cast, or injection molded. In some embodiments, the components may be made using 3D printing or other additive manufacturing techniques commonly used in the art. In some embodiments, the materials can withstand commonly used sterilization techniques. In some embodiments, the implant devices are constructed from a biocompatible material including but not limited to stainless steel, titanium, nitinol, and combinations and composites thereof.

In some embodiments, the flexible implant device 100 includes a longitudinal internal through hole. In some embodiments, an endoscopic camera can be embedded or passed through the internal though hole to provide an internal anatomical view to a clinician utilizing the device in a surgical setting, providing information on the quality of the tapping and the quality of the bone that is being tapped. In some embodiments, sensors can be embedded in the flexible implant device 100 to create a smart implant. These sensors can include strain gauges and optical fibers to dynamically measure the forces on the implant during and after implantation using a wireless sending and receiving module.

U-Bridge Implant Device

Figure 6A:
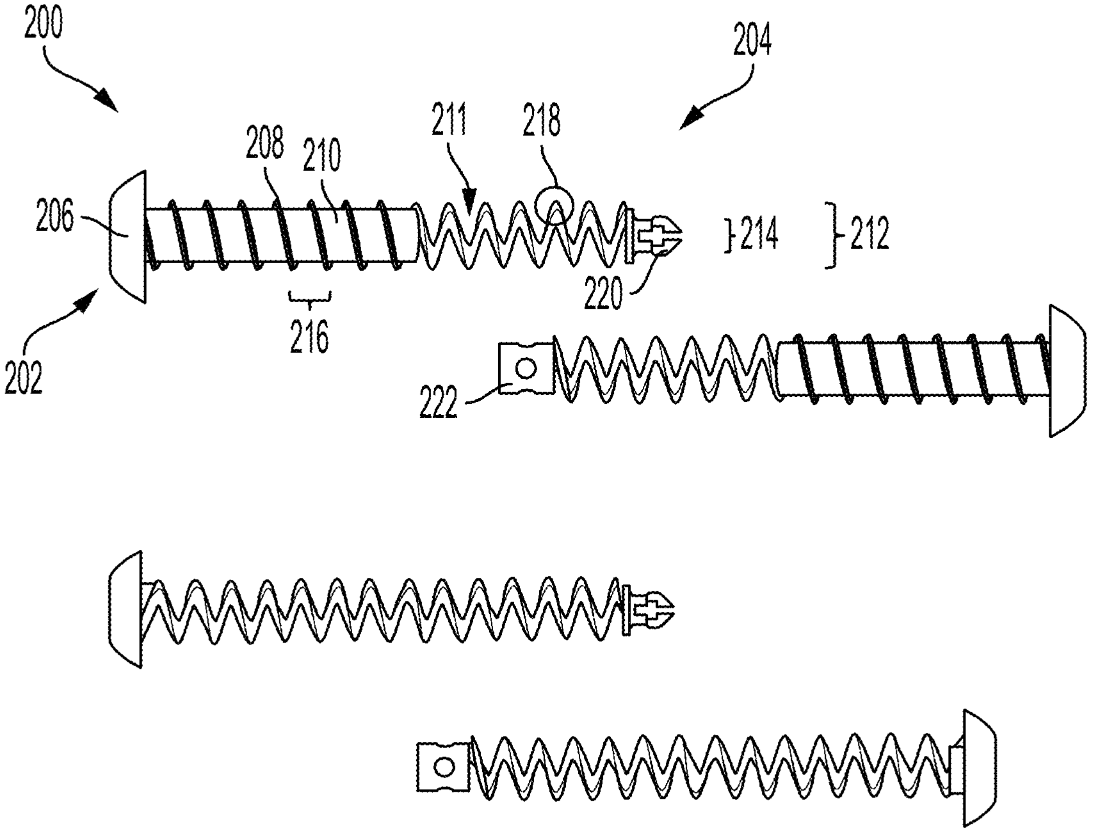
FIG. 6A through FIG. 6B depict exemplary U-bridge implant devices.
Figure 6B:
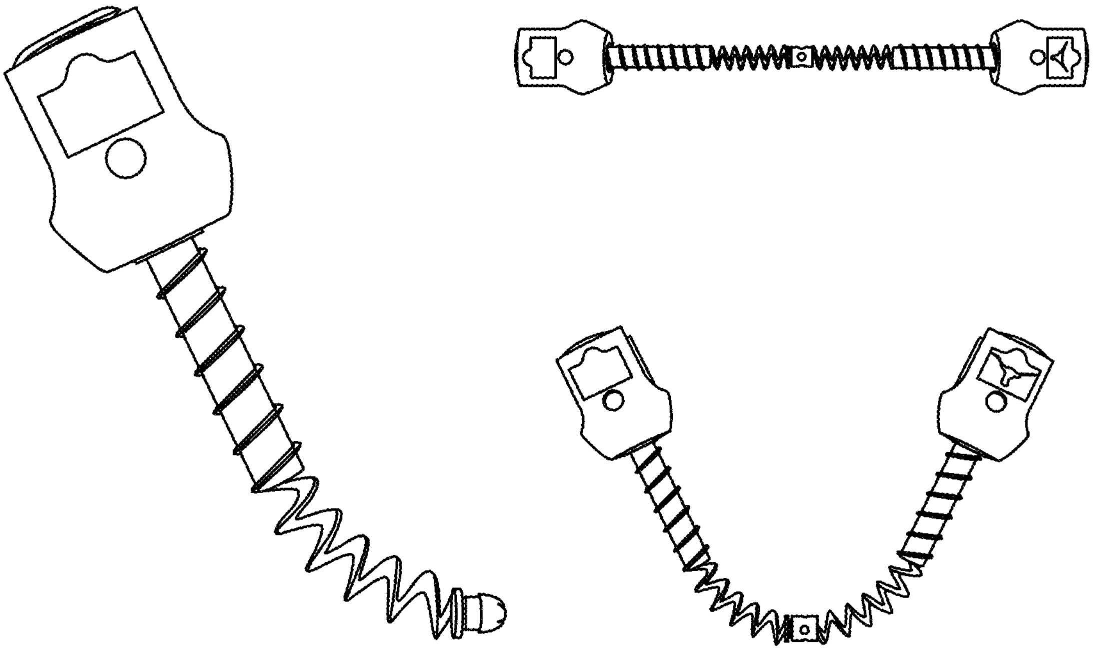

Referring now to FIG. 6A through FIG. 6B, exemplary U-bridge implant devices 200 are depicted. Device 200 comprises a length extending between a proximal end 202 and a distal end 204. Device 200 comprises a driving head 206 at proximal end 202, a rigid shank 210 extending towards distal end 204 for a portion of the length, and a flexible engagement member 208 extending from shank 210 to a tip 220 at distal end 204. In some embodiments, driving head 206 can be adapted for spinal fixation similar to traditional pedicle screws, as shown in FIG. 6B. Tip 220 can be any suitable tip, such as a self-tapping tip, a blunt tip, and a sharp tip. In some embodiments, tip 220 is a mating connector configured to connect to a complementary tip 222, such that distal ends of two devices 200 may be secured together. Engagement member 208 thereby is at least partially formed around a shank-less space 211. In some embodiments, device 200 is completely shank-less, as shown in the lower image of FIG. 6A.

Engagement member 208 forms a spiral, helical, or spring-like shape and is at least partially formed around a shank-less space 211. Engagement member 208 comprises an outer facing surface configured to grip onto an implant site, wherein the outer facing surface comprises an engagement structure including but not limited to a screw thread (FIG. 6A), a knurling pattern (FIG. 3, left), a grating pattern (FIG. 3, right), and combinations thereof. In some embodiments, engagement member 208 extends for at least a portion over a length of shank 210. In some embodiments, engagement member 208 extends for the entire length of shank 210 and reaches driving head 206. Accordingly, device 200 comprises at least one rigid portion corresponding to a length of shank 210 and at least one flexible portion corresponding to a length of engagement member 208 that is free from shank 210.

Engagement member 208 has an outer diameter 212, an inner diameter 214, and a cross-sectional shape 218. Outer diameter 212 can be any suitable size, such as in a range between about 1 and 10 mm, as well as a variable size along the length of device 200 between about 1 and 10 mm. In some embodiments, engagement member 208 comprises a constant outer diameter 212, such that device 200 comprises a substantially cylindrical shape. In some embodiments, engagement member 208 comprises a variable outer diameter 212, such that device 200 comprises a substantially conical shape wherein a proximal outer diameter 212 is wider than a distal outer diameter 212. In various embodiments, device 200 comprises a combination of sections having a constant outer diameter 212 and sections having a variable outer diameter 212. Inner diameter 214 can be any suitable size, such as in a range between about 0 and 9 mm, as well as a variable size along the length of device 200 between about 0 and 9 mm. In some embodiments wherein engagement member 208 is a screw thread, engagement member 208 can further comprise a thread pitch 216. Thread pitch 216 is a measure between adjacent threads, and can be any suitable size, such as in a range between about 0.1 and 5 mm, as well as a variable size along the length of device 200 between about 0.1 and 5 mm. While the exemplary device 200 is depicted in FIG. 6A as having a substantially triangular cross-sectional shape 218, it should be understood that device 200 can have any cross-sectional shape 218, including but not limited to square shapes, pentagon shapes, hexagon shapes, rectangular shapes, rhombus shapes, diamond shapes, trapezoid shapes, and the like. Cross-sectional shape 218, as well as the size of cross-sectional shape 218, can also be variable along the length of device 200. In some embodiments, the varying cross-sectional shapes described above are equally applicable to shaft 210 and inner diameter 214.

Figure 7A:
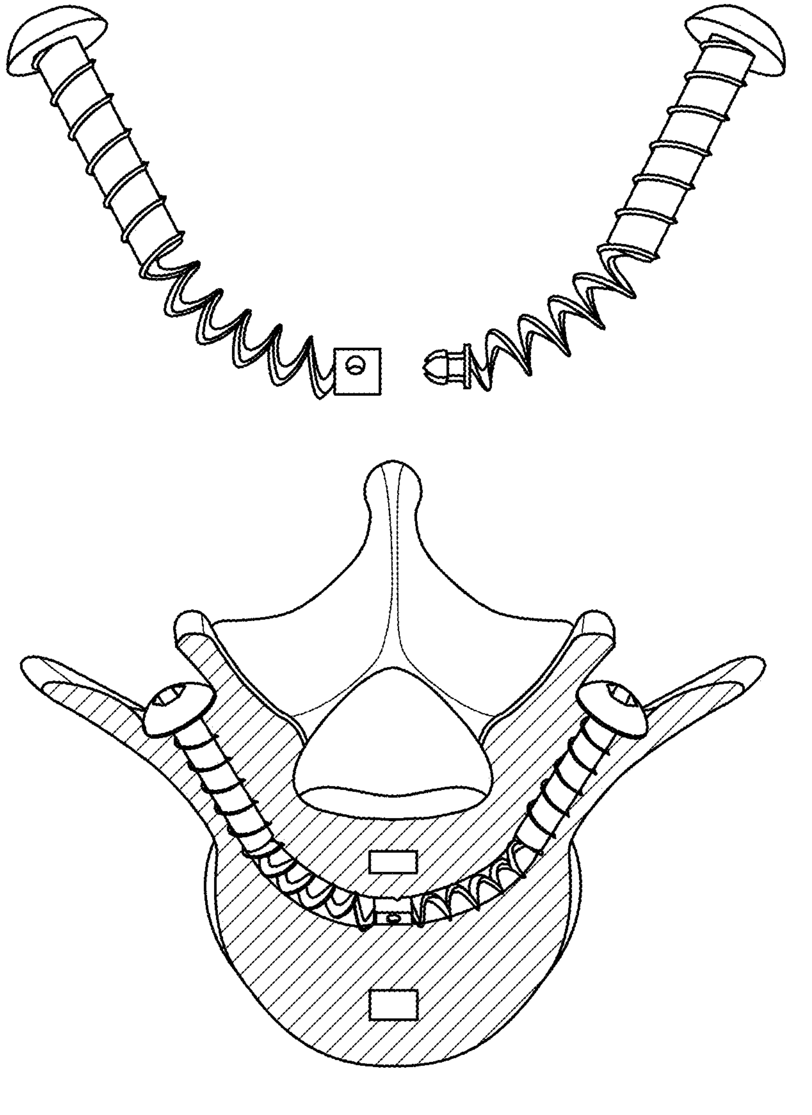
FIG. 7A and FIG. 7B depict schematics of a paired U-bridge implant device.
Figure 7B:
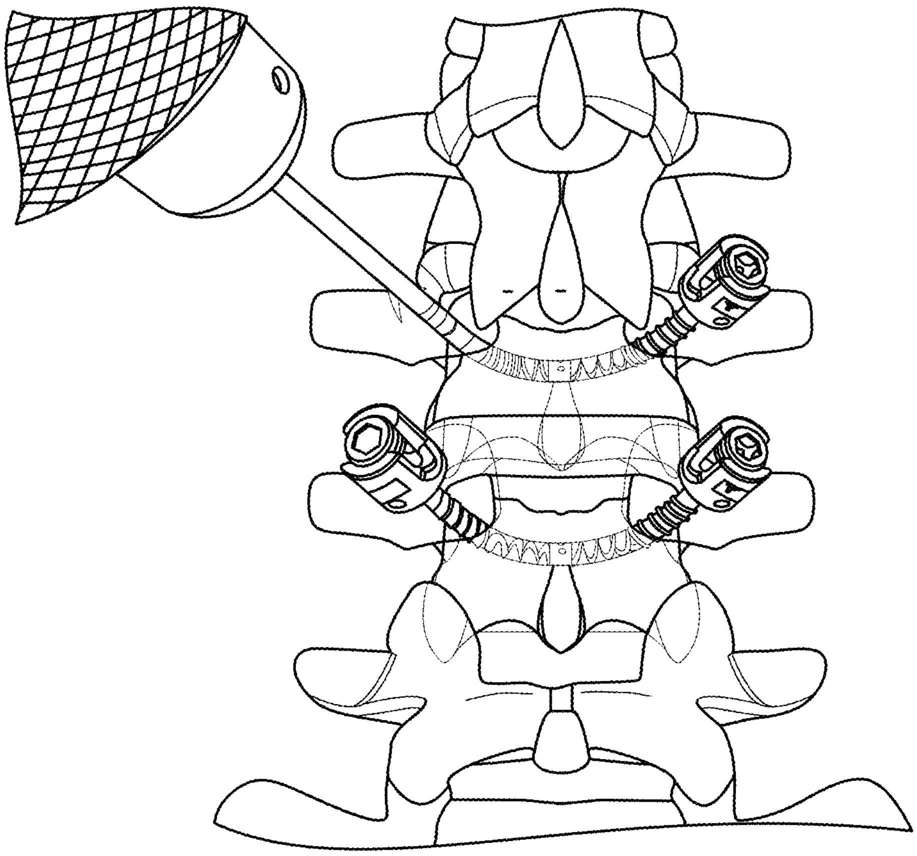

In some embodiments, the U-bridge implant devices are provided in a series of preset dimensions and shapes. In this manner, an appropriate U-bridge implant device may be selected at the time of use, which may be a single U-bridge implant device that is configured to span an entire target tissue, or may be two U-bridge implant devices that are configured to fit into a target tissue and lock together there (FIG. 7A). In some embodiments, the U-bridge implant devices of the present invention are tailored in that the devices are fabricated with dimensions and shapes based on the characteristics of a subject and are specific to a subject. As described elsewhere herein, the U-bridge implant devices comprise several components having dimensions and shapes that that may be selected from a range, including but not limited to shank length, engagement member length, screw thread pitch (where engagement member is a screw thread), engagement member outer diameter, engagement member inner diameter, engagement member cross-sectional shape, and tip. Characteristics of a subject that may determine the specific construction of a U-bridge implant device include but are not limited to: bone anatomy, surgical application, bone mineral density, bone mineral distribution, cortical bone thickness, cancellous bone thickness, curvature of a drilling trajectory, plane of insertion in to bone, and the like. A U-bridge implant device specific to a subject may then be fabricated having a specific shank length, thread length, thread pitch, thread outer diameter, thread inner diameter, and/or thread cross-sectional shape to form the curvatures necessary to conform to the characteristics of the subject.

As described elsewhere herein, device 200 can be mated to one or more additional devices 200. The joining of multiple devices 200 can form an overall U-shape Each device 200 can comprise a tip 220 configured to mate to a tip 222 or to a driving head 206, wherein each device 200 can be used interchangeably to mate to additional devices 200. In some embodiments, a single device 200 can be used to form an overall U-shape. Exemplary configurations are shown in FIG. 8A through FIG. 8C. In FIG. 8A, a solitary device 200 is implanted as a single continuous implant. In FIG. 8B, a first device 200*a* is implanted end-to-end with a second device 200*b*, wherein tip 220*a* mates with tip 222*b*. In FIG. 8C, a first device 200*a*, a second device 200*b*, and a third device 200*c* are implanted end-to-end, wherein tip 220*c* mates with and/or drives driving head 206*a* and tip 220*a* mates with tip 222*b*. It should be understood that any desired number of devices 200 may be used in combination, and each device 200 in a combination may comprise the same or different attributes as described elsewhere herein (shank length, engagement member length, screw thread pitch (where engagement member is a screw thread), engagement member outer diameter, engagement member inner diameter, engagement member cross-sectional shape, and the like).

While exemplary U-bridge implant devices of the present invention are described above, the U-bridge implant devices are nonetheless amenable to any suitable modification to augment their function. For example, in various embodiments, the U-bridge implant devices can include one or more surface coatings that are configured to enhance pullout strength, biocompatibility, or both. Contemplated coatings include but are not limited to PEEK, PTFE, hydroxyapatite, and the like. In some embodiments, the U-bridge implant devices can accept a bone cement. Sections of the U-bridge implant devices that are shank-less can receive a bone cement injection within an inner diameter that can set after implantation to improve rigidity and pullout strength. In some embodiments, sections of the U-bridge implant devices that include a shank can further comprise a lumen within the shank to facilitate the injection of a bone cement into the shank-less sections. In various embodiments, the implant devices can be further reinforced by the insertion of one or more wires into the shank-less sections.

The U-bridge implant devices of the present invention can be made using any suitable method known in the art. The method of making may vary depending on the materials used. For example, components substantially comprising a metal may be milled from a larger block of metal or may be cast from molten metal. Likewise, components substantially comprising a plastic or polymer may be milled from a larger block, cast, or injection molded. In some embodiments, the components may be made using 3D printing or other additive manufacturing techniques commonly used in the art. In some embodiments, the materials can withstand commonly used sterilization techniques. In some embodiments, the implant devices are constructed from a biocompatible material including but not limited to stainless steel, titanium, nitinol, and combinations and composites thereof.

In some embodiments, the U-bridge implant device 200 includes a longitudinal internal through hole. In some embodiments, an endoscopic camera can be embedded or passed through the internal though hole to provide an internal anatomical view to a clinician utilizing the device in a surgical setting, providing information on the quality of the tapping and the quality of the bone that is being tapped. In some embodiments, sensors can be embedded in the U-bridge implant device 200 to create a smart implant. These sensors can include strain gauges and optical fibers to dynamically measure the forces on the implant during and after implantation using a wireless sending and receiving module.

Methods of Enhanced Tissue Fixation

The present invention also relates to methods of enhanced implant fixation using the flexible implant devices and/or U-bridge implant devices described herein. The methods improve implant fixation by implementing biomechanical analysis in a target tissue that maps bone mineral density and planning an implant trajectory that maximizes implant fixation in regions of high bone mineral density (FIG. 11).

Referring now to FIG. 12, bone mineral density in a target tissue is measured using quantitative computed tomography (QCT) along with a calibration phantom positioned near a subject. The calibration phantom comprises regions of known Hounsfield units that appear darker with lower densities and lighter with higher densities. Using the calibration phantom, the bone mineral density of the target tissue can be quantified. In FIG. 13, the workflow of converting a series of QCT images to a biomechanical model of the vertebra is shown. QCT images are segmented and a three-dimensional finite element model is constructed based on them such that each element of the model has the material property of the corresponding voxel in the QCT images. The three-dimensional model can then be used to design and analyze a custom flexible implant device, including but not limited to implant path, material, shape, etc. Furthermore, it can demarcate osteoporotic regions and low bone mineral density regions of the target tissue (FIG. 14) for which possible implant trajectories may avoid (FIG. 15). While osteoporotic regions may be defined as having a bone mineral density of less than 80 mg/cm$^3$, it should be understood that any threshold may be used. For example, regions of bone mineral density may be characterized as low relative to the surrounding tissue, such that an optimal implant trajectory favors the higher density tissue over the lower density tissue, even if the lower density tissue has a bone mineral density greater than 80 mg/cm$^3$. An optimal implant trajectory (FIG. 16) may avoid osteoporotic regions and low bone mineral density regions, resulting in minimized strain and improved pullout strength when compared to conventional linear screw paths (FIG. 17) that are unable to evade osteoporotic regions and low bone mineral density regions. In some embodiments, the implant trajectory can be configured to extend into an adjacent cortical bone (FIG. 18), such that a flexible implant device can be driven into the adjacent cortical bone to enhance fixation strength and stability.

Experimental Examples

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out exemplary embodiments of the present invention, and are not to be construed as limiting in any way the remainder of the disclosure.

FIGS. 22 through 27 depict exemplary experimental devices, setups, and results for exemplary flexible implant devices. The guiding principle behind the usage of a pedicle screw is to fix broken bones back into place after they have experienced a fracture. The flexible implant device comprising a flexible pedicle screw (FPS) must be designed taking into account all of the geometrical properties affecting the overall capability of the screw while considering safety and screw feasibility in the spine. The FPS must also take into consideration both internal and external constraints that affect it such as the drilling tools.

The typical process of creating a trajectory for rigid pedicle screw fixation is the utilization of a rigid, linear trajectory drill by the surgeon to create a tunnel for the screw placement. To maximize the capabilities of the FPS, a drill capable of creating properly sized, curved trajectories needs to be available.

The steerable drilling robot (SDR) illustrated by Sharma et al. is a major guiding factor for the design of the FPS. The SDR is a three-component robot with two of the components being the external and internal tubing. The external concentric tubes act as steering cannula while providing structural integrity for the overall device and providing housing for the flexible inner component. The flexible inner component drills into the bone to create a trajectory for the FPS.

Furthermore, the external tubing is made of 2 different tubes, a rigid stainless steel tubing that is 80 mm long with a 3.175 outer diameter (OD), and a NiTi tubing attached to the stainless steel tubing that is 3.61 mm long and has a wall thickness of 0.25 mm. The inner tubing consists of an drill bit at the tip, a torque coil in the middle, and a straight shaft at the end. Two drill bits (42955A35, McMaster-Carr and 8878A42, McMaster-Carr) are capable of being used with this device, with both having a diameter between 6 and 7 mm. The torque coil is located between the drill bit tip and the straight shaft end. The torque coil was of 70 mm length (Asahi Intec. USA, Inc.) and 2.33 mm OD while the straight shaft end had a diameter of 1.56 mm OD. The performance and efficacy of the system has been successfully validated by Sharma et al. (S. Sharma, T. G. Mohanraj, J. P. Amadio, M. Khadem, and F. Alambeigi, "A steerable drilling robot for minimally invasive spinal fixation of osteoporotic vertebrae."), incorporated herein by reference in its entirety.

The FPS' ability to safely follow the curved trajectory created by the SDR is needed for practicality. The rounded head tip allows for safe usage of the screw inside the vertebra during the surgery process by allowing for a lower friction interaction between the screw head and the bones it will be interacting with, as shown in FIGS. 22A-B, while following the curved trajectory. The internal stability of the screw plays a larger role in the safety of the screw. Optimization between the different screw geometries, such as the inner and outer diameter, as well the screw's flexible and rigid region are configurable for safe bending. The inclusion of a flexible and rigid region in the screw also plays a role in the user safety. The inclusion of the rigid region allows for a reduction in bending stress compared to previous screw models via a decrease in length while decreasing possible instability that a fully flexible screw might provide in a rigid, straight pedicle region.

In some embodiments, the FPR comprises sharper threads allowing for smoother bone fixation in order to decrease operation time and provide stronger fixation inside the bone from the FPS. In some embodiments, the FPS has a self-tapping capability contributing to better fixation inside the bone, see Shea et al. (T. M. Shea, J. Laun, S. A. Gonzalez-Blohm, J. J. Doulgeris, W. E. Lee 3rd, K. Aghayev, and F. D. Vrionis, "Designs and techniques that improve the pullout strength of pedicle screws in osteoporotic vertebrae: current status," BioMed research international, 2014), incorporated herein by reference in its entirety. FIGS. 22A-B highlight the first couple threads in the screw having these sharp edges to carve the threaded path for the rest of the screw, see Alambeigi et al., (F. Alambeigi, M. Bakhtiarinejad, A. Azizi, R. Hegeman, I. Iordachita, H. Khanuja, and M. Armand, "Inroads toward robot-assisted internal fixation of bone fractures using a bendable medical screw and the curved drilling technique," in 2018 7th IEEE International Conference on Biomedical Robotics and Biomechatronics (Biorob). IEEE, 2018, pp. 595-600), incorporated herein by reference in its entirety.

The FPS also includes certain design considerations that allow for enhanced internal fixation between the bone and the screw. The FPS's internal fixation ability is augmented by the inclusion of cannulated regions in the rigid and flexible part of the screw as well as the tip of the screw. This cannulated region along with the flexible part allows for better bio-integration by leaving areas for bone formation within the screw. The inclusion of the cannulated regions also further gives the option of increasing internal fixation augmentation via the capability of injecting PMMA (e.g. bone cement) within the cannulated region of the screw. This, in turn, allows for an option to increase the prevention of screw pullout phenomena from occurring while increasing the efficacy and strength of the screw fixation within the body. The inclusion of the cannulated region within the rigid end of the screw allows for similar reduction in the bending stress on the flexible end as a solid body rigid end while increasing the opportunity for better internal fixation.

Multiple different FPSs were initially designed with different design considerations such as varying pitch and diameter. These screws were then analyzed using FEA with two screw designs of differing parameters being further fabricated and analyzed experimentally furthering exemplifying the capability of the design and fabrication process.

Stainless Steel 316L was chosen as the screw material of choice due to its bio-compatibility, popularity as a material for permanent implant design, and case-of-manufacturing via the metal additive manufacturing process. The FPS, as shown in FIGS. 22A-B, was designed with a semi-flexible semi-rigid combination in mind in order to minimize bending stress at the end of the flexible part while increasing support in the pedicle structure of the vertebra. The screw properties were designed around the initial capabilities shown by the drill discussed in the paper by Sharma et al. Initial capabilities of the drill showed the average hole size to be 8 mm in diameter due to drill properties and external vibrations. Therefore, a screw was designed with a 9 mm outer diameter (OD) and a 6 mm inner diameter (ID) along with a V-shape screw thread. The screw thread height, 1.5 mm, and thread shape was chosen to maximize sharpness in order to ensure a smoother insertion process. The first four threads were also created with self-tapping capabilities in order to minimize operation time and maximize pullout strength. There were a total of 11 threads on the screw overall. The pitch of about 4 mm was chosen to allow sufficient space for efficient bone growth while also allowing for adequate bending capabilities. The overall length came out to be about 57.14 mm with the rigid part being 26.81 mm and the flexible part being 30.83 mm. The screw is also cannulated in order to provide access for the injection of polymethylmethacrylate (PMMA) in order to maximize biointegration and pull-out strength. The screw sizes mentioned above are easily able to be manipulated to best fit the patients and surgeons needs with a fabricated example of a smaller screw being shown in FIG. 24. The smaller screw was designed with the same considerations in mind with the screw having a 6 mm OD and a 3 mm ID with 1.5 mm deep, V-shape threads. The 6 mm OD screw has an overall length of 52.55 mm with the rigid region being 22.49 mm and the flexible region being 30.11 mm. The smaller screw has 16 threads with a pitch of 2.857 mm between them. This screw was designed to match the size of more common pedicle screws in the market. The thread thickness for both screws was 1 mm for the best fabrication results. In order to understand the FPSs capability under insertion and bending, two different FEAs were conducted on the screw using ANSYS Workbench. The FPS bending and torsion capabilities were verified using the static structural analysis in ANSYS Workbench. The screw was modeled using orthotropic material properties with the appropriate constitutive equation stated in Voigt notation as follows:

$$\begin{Bmatrix} \epsilon_1 \\ \epsilon_2 \\ \epsilon_3 \\ \epsilon_4 \\ \epsilon_5 \\ \epsilon_6 \end{Bmatrix} = \begin{bmatrix} 1/E_1 & -\upsilon_{21}/E_2 & -\upsilon_{31}/E_3 & 0 & 0 & 0 \\ -\upsilon_{12}/E_1 & 1/E_2 & -\upsilon_{32}/E_3 & 0 & 0 & 0 \\ -\upsilon_{13}/E_1 & -\upsilon_{23}/E_2 & 1/E_3 & 0 & 0 & 0 \\ 0 & 0 & 0 & 1/G_{23} & 0 & 0 \\ 0 & 0 & 0 & 0 & 1/G_{31} & 0 \\ 0 & 0 & 0 & 0 & 0 & 1/G_{12} \end{bmatrix} \begin{Bmatrix} \sigma_1 \\ \sigma_2 \\ \sigma_3 \\ \sigma_4 \\ \sigma_5 \\ \sigma_6 \end{Bmatrix} \tag{1}$$

where $\epsilon$ and $\sigma$ represents the strain and stress, respectively. E, G, and $\nu$ represents the Young's modulus, shear modulus, and Poisson's ratio, respectively.

The Young's modulus was derived from the literature and the additive manufacturing machines guide while constant Poison's ratio and shear moduli were used from previous reported values for these constants as well as not being substantially affected by the metal additive manufacturing process, see Tilton et al. (M. Tilton, G. S. Lewis, H. B. Wee, A. Armstrong, M. W. Hast, and G. Manogharan, "Additive manufacturing of fracture fixation implants: Design, material characterization, biomechanical modeling and experimentation," Additive Manufacturing, vol. 33, 2020), Feng (R. Feng, "Material characterization of additive manufactured metals using a line-focus transducer system," Master's thesis, University of Pittsburgh, 2021), and (*EOS Stain-*

Figure 23C:
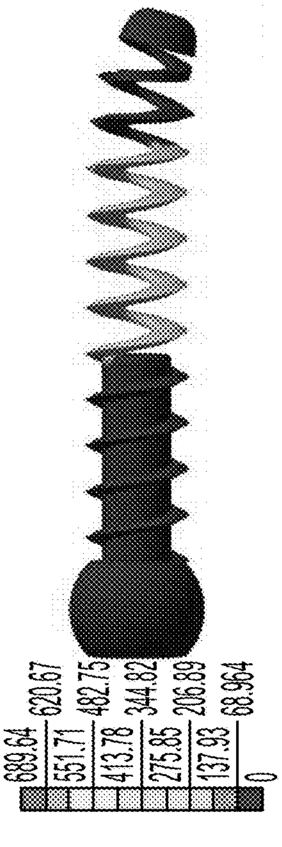
Figure 23D:
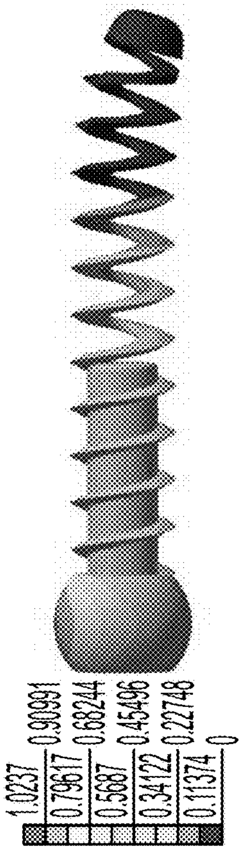

*lessSteel* 316L, EOS, 2014), each incorporated herein by reference in their entirety. These simulations were used to assess the validity of the initial FPS design. FIGS. 23A-D show the FEA results for the screw undergoing two different torsion conditions to illustrate the screw thread stability under the tapping process after the desired fixation has been reached. The first torsion condition (FIGS. 23A-B) illustrates when the last two threads aren't fixed inside the vertebra, while the second torsion condition (FIGS. 23C-D) illustrates only the first two threads fixed inside the vertebra. The former is when the screw faces the maximum frictional force for screw insertion while the latter is when the screw needs to start the tapping process. The screw was assumed to be homogeneous, elastic, linear, and orthotropic with a Young's modulus of 185 GPa in the XY direction and 180 GPa in the Z direction. It was also assumed to have a Poisson's ratio of 0.234 and a shear modulus of 62 GPa. A nonlinear mechanics physics preference was utilized to generate a finer, quadratic mesh in ANSYS workbench with an element size of 0.6 mm. The respective threads on the screw were already assumed to be in a bent shape matching the bend angle of the drill created by Sharma et al. within the vertebra during this simulation. In the simulation, the screw threads were respectively fixed to illustrate the correct fixation step in tapping processes, and the maximum torsion was applied so that it was still beneath the ultimate tensile strength of 690 MPa. FIGS. 23A-B show the screw with all but the last two threads being fixed inside the vertebra can take a maximum torsion of 0.246 Nm while undergoing a deformation of 0.403 mm. FIGS. 23C-D show that the screw where only the first two threads were fixed inside the vertebra can take a maximum torsion of 0.232 Nm while facing a strain of 0.00547 on the head of the screw indicating negligible distortion. The same simulation was conducted for the 6 mm screw where the maximum torsion of 0.01475 Nm could be applied when the entire screw except for the last two threads were inside while undergoing a deformation of the 0.0305 mm. When only the first two threads of the 6 mm screw were inside the vertebra, a maximum torsion of 0.0149 Nm could be applied to get a maximum deformation of 0.112 mm at the head of the screw.

Figure 23E:
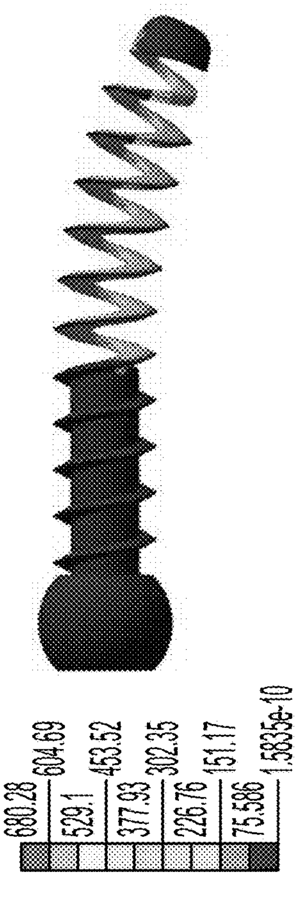
Figure 23F:
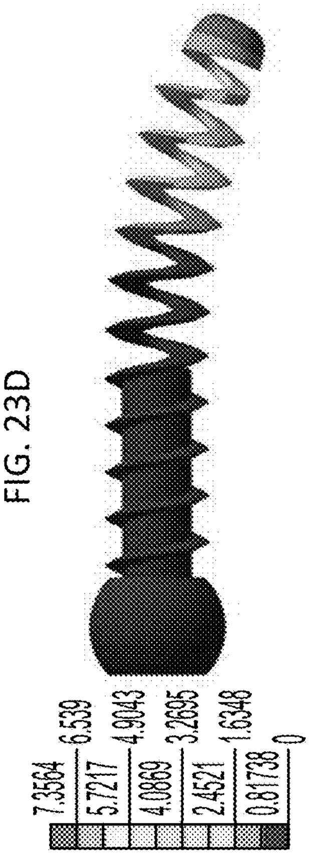

FIGS. 23E-F illustrate the stress and displacement of a screw deformed to its maximum bending angle of 27 degrees under its ultimate tensile strength. This simulation is performed to illustrate the screw's capability to be bent to match realistic bending conditions that it will be expected to face in its medical usage. The rigid part of the screw is fixed to illustrate real world conditions with a rotational displacement condition being added to tip to illustrate the deformation capabilities with large deformation capabilities being utilized for this simulation. The screw is assumed to have the same material properties as described in the torsion-tapping section being a homogeneous, elastic, linear and orthotropic. A maximum bending stress of 680 MPa and a deformation of 7 mm is witnessed under these conditions for the 9 mm OD screw. The 6 mm screw was capable of being bent to an approximate maximum bending angle of 7 degrees which leads to an about a 2 mm tip deformation while staying under the ultimate tensile strength. It is notable that these values only illustrate the maximum bending capability of the screws under elastic conditions with the screw being capable of being utilized under plastic deformation conditions in real world operations. The initial estimates are useful, however, and provide us with a fundamental data for future designs.

FIG. 24 illustrates the completed additive manufactured parts made from SS 316L granulates sourced from EOS (Krailling, Germany) on a build plate with two separate designs of the FPS. The first screw show on the left illustrates the smaller screw design mentioned earlier with the larger screw adjacent. The screws were built on the same build plate with multiple stainless steel supports supporting each thread and screw tip for the prevention of residual stress effects. EOS companies' software and M280 machine were used in parallel due to compatibility capabilities. A Direct Metal Laser Splintering (DMLS) manufacturing process was used to conjoin the stainless steel 316L granulates under an inert argon atmosphere. A layer thickness of 20 microns was prescribed to be added at each pass of the fusing process.

The print was built in a diagonal manner to make support removal easier from the 1 mm thick threads. After the supports on the print were removed using hand tools, the print was cleaned using a sand-blasting tool to remove any surface imperfections and create a clean final product as shown on the right. The entire fabrication and post-processing process of the flexible screw took around 27 hours to complete.

In order to get accurate and continuous force placed on the screw under variable displacement, a testing fixture along with a linear stage and load cell were used to get a force-displacement relationships as illustrated in FIG. 25. A testing fixture to constraint the screw was created using Solidworks (Waltham, Massachussetts) and printed using Raise3D E2 printer (Costa Mesa, California). A single-row linear stage (MUMR 12.40, Newport) with 1 μm precision was used to gather displacement of the screw. The linear stage would lead to 1 mm displacement for a full 360 degree rotation of the handle. An digital force gauge (Mark-10 Series 5, Mark Ten) with 0.02N resolution was used to place a force on the tip of the screw. The linear stage and the force gauge are coupled together for better accuracy. The testing fixture was screwed to the optical table with the screw fixated inside of it. There were an additional two screws used to conjoin the top and bottom part of the testing fixture together.

To obtain a realistic image of the capabilities of the designed and simulated screw, an insertion scenario was created using the following set-up. A 10 PCF polyurethane foam block (Sawbones; Pacific Research Laboratories, Washington, USA) was also used for insertion testing purposes as a substitute for human cancellous bone. A C-arm (OEC One CFD, GE Healthcare; Chicago, Illinois) x-ray machine was also used in parallel to get pictures of the screw during the insertion process. To simulate a surgical insertion, several curved trajectories were first drilled through the polyurethane sample piece using a Steerable Drilling Robot (SDR). The SDR takes advantage of the superelastic properties of nitinol to create exchangeable steering cannula nested within one another to guide a drill bit in controlled directions. For this experiment, the SDR was set-up with pre-selected steering cannula to create a straight hole with a depth of 20 mm, followed by a tangential curved path with a 35 mm radius for the flexible screw to follow. The diameter of the drilled holes was approximately 7.5 mm, allowing for a thread depth of 0.75 mm. After the path was drilled, the screw was aligned with the entrance and manually inserted into the sample. Throughout the insertion, images were taken using the c-arm x-ray system to view the screw's performance.

Due to the importance of FEA in the development of the FPS, an in-depth experimental study validating the FEA results against experimental results was conducted utilizing the single row linear stage and the force gauge machine mentioned previously. The overall goal was to measure the efficacy and capability of the simulation to match real world results regarding tip displacement of the screw under continuous load application.

The overall goal of the screw insertion test was to witness the screw's self-tapping capability while being inserted into the synthetic bone along with the FPS's capability of following a curved trajectory created by the SDR.

In order to evaluate the FPS tip displacement capabilities under variable load, force-displacement experiments were conducted utilizing a side-view camera system, a single-row linear stage, a force gauge, and a testing fixture to house the rigid part of the screw. The testing fixture was a two-part component joined together with smaller bolts as illustrated in FIG. 25.

A testing fixture was prepared for the respective screw being tested with the two halves of the testing fixture being bolted together after the FPS had been placed inside in order to create a constraint for the FPS. The tip of the force gauge was brought slowly down via the linear stage till the force gauge barely touched the tip of the screw. The side camera was utilized during this process to detect when the two tips met. After the tips met, the force gauge was zeroed out and the linear stage was rotated in 0.5 mm increments up to 6 mm therefore imposing a 6 mm tip displacement on the screw tip. FIG. 25 illustrates the trajectory of the 9 mm OD screw under the 6 mm displacement. The force gauge was then moved upward till there was no visible interaction between the screw tip and the force gauge tip. The experiment was then repeated three times with the results being averaged out, with the same experiment being performed for the 6 mm screw. FIGS. 26A-B show the obtained experimental forces needed to displace the tips by 0.5 mm overlaid with the FEA.

An FEA model was then established to understand the relationship between the simulation and experimental results for both screws. The screw was modeled as homogeneous, elastic, linear, and orthotropic using the same constitutive relationship mentioned above. Varying Young's modulus were used from 150 GPa to 180 GPa in the XYZ direction in order to capture the correct data point displacements from the experiment with the shear modulus and Poisson's ratio of 60 GPa and 0.234 being used, respectively. A tensile yield strength of 590 MPa and an ultimate tensile strength of 690 MPa were assumed during the simulation process. A non-linear mechanics physics preference was utilized to generate a finer, quadratic mesh in ANSYS workbench with the element mesh size being 0.6 mm. Large deflection was also utilized for these models in order to capture the most accurate force results. The model had similar boundary conditions as the simulations shown in FIGS. 23A-F. The rigid end of the screw was fixed to illustrate the experimental conditions with displacements of 0.5 mm up to 6 mm being added every second to the screw tip. FIGS. 26A-B illustrate the relationship between the experiment and the simulation models.

In order to accomplish this experiment, a curved trajectory tunnel was created within the synthetic bone. This was done by creating a straight hole that matched the length of the rigid part of the FPS; then the SDR was used to create a 35.7 mm radius of curvature hole that would be the trajectory the FPS would follow during the insertion process. After the curved tunnel was created, the in-house x-ray machine was placed in a proper location that would allow for clear visualization of the screw insertion process. The screw was then inserted into synthetic bone with FIGS. 27A-F illustrating the full FPS insertion process with the screw reaching a final bend angle 30.8 degrees in FIG. 27F. This experiment illustrated the self-tapping capability of the screw along with the FPS's capability of bending to match the trajectory created by the SDR. The angle is also an approximate match for the maximum bending angle illustrated in the FEA in FIGS. 23E-F.

The results illustrate that the simulation model closely follows the experimental model in terms of mean average error for both screw models with the maximum mean average error being less than 17% for the 180 GPa Young's modulus. As predicted, at a higher theoretical Young's modulus, the amount of force necessary to bend the screw to the same tip displacement is higher. FIG. 26A illustrates the displacement of the 9 mm screw tip under varying loads, ultimately requiring around 3.55 newtons (N) of force to reach the maximum displacement of 6 mm. These results were closely matched by the all the theoretical Young's modulus simulated with quite clear overlaps between the other models till the 4 mm displacement mark. Around the 4 mm mark, the theoretical models tend to illustrate that more force is required to bend the screw to the same displacement as experimentally shown. The 150 GPa Young's modulus matched the values the best with a mean average error of 7.127% with the 180 GPa Young's modulus simulation having an mean average error of 16.571%. The theoretical Young's modulus of 160 and 170 GPa saw respective mean average errors of 10.840% and 13.336%. These errors match the overall expected trend since a decrease in stiffness would lead to less force being required to bend the FPS to the same tip displacement condition as experimentally expected. The results for the 6 mm screw also match the overall expected results. As predicted, the 6 mm screw also required less force overall to reach the same tip displacement of the 9 mm due to a smaller cross-sectional area providing less resistance to bending. The theoretical Young's modulus also follow a similar trend as the 9 mm screw where the experimental and theoretical values of the screw match up quite accurately till the 4 mm mark where major divergence occurs. The experimental models leads to illustrate that the theoretical models need more force to bend the screw to the same displacement as experimentally shown—a trend similar to the 9 mm screw as well. The 150 GPa Young's modulus matched the values the best with a mean average error of 9.577% with the 180 GPa Young's modulus simulation having an mean average error of 16.803%. The theoretical Young's modulus of 160 and 170 GPa saw respective mean average errors of 12.285% and 14.674%. These errors match the overall expected trend since a decrease in stiffness would lead to less force being required to bend the FPS to the same tip displacement condition as experimentally expected. Furthermore, another observation that can be made regarding this experiment is the linearity that can be seen in both the theoretical and experimental aspect. This allows for finding the force required for the screw to reach higher bending angles. Another observation that can be made is that, other than a slight decrease made in the shear moduli from 62 GPa to 60 GPa, the majority of the tuning was focused on changing the theoretical Young's modulus to match the desired bending angle. Significantly, an entire model tuning would lead to an optimized version for the screw.

The results for the self-insertion test indicates the screw's capability to reach necessary bending angles while also validating the threads self-tapping potential. FIGS. 27A-F illustrate the insertion process for the screw and illustrates how it can bend to match a previously curved trajectory created by the SDR. Note that even after the screw insertion and extraction process, the screw keeps the same shape as before indicating a lack of plastic deformation while bending to the predicted bending angle of the FEA from FIGS. 23E-F. This illustrates the shape-adaptability of the screw while also validating the self-tapping capability.

The following references are included herein by reference in their entireties:

N. C. Wright, A. C. Looker, K. G. Saag, J. R. Curtis, E. S. Delzell, S. Randall, and B. Dawson-Hughes, "The recent prevalence of osteoporosis and low bone mass in the united states based on bone mineral density at the femoral neck or lumbar spine," *Journal of Bone and Mineral Research*, vol. 29, no. 11, pp. 2520-2526, 2014.

R. Burge, B. Dawson-Hughes, D. H. Solomon, J. B. Wong, A. King, and A. Tosteson, "Incidence and economic burden of osteoporosis-related fractures in the united states, 2005-2025*," Journal of bone and mineral research*, vol. 22, no. 3, pp. 465-475, 2007.

E. L. et al, "Healthcare policy changes in osteoporosis can improve outcomes and reduce costs in the united states," *JBMR plus*, vol. 3, no. 9, 2019.

"Raising awareness to strengthen bone health: 2018 annual report." National Osteoporosis Foundation (NOF). [Online]. Available: http://www.bonehealthandosteoporosis.org/wpcontent/uploads/2018$_{N}$OF$_{A}$nnual$_{r}$eport$_{F}$IN AL.pdf G. F. Anderson and P. S. Hussey, "Population aging: A comparison among industrialized countries: Populations around the world are growing older, but the trends are not cause for despair." *Health affairs*, vol. 19, no. 3, pp. 191-203, 2000.

Osteoporosis fast facts. [Online]. Available: www.nof.org

C. Klotzbuecher, P. Ross, P. Landsman, T. Abbott III, and M. Berger, "Patients with prior fractures have an increased risk of future fractures: a summary of the literature and statistical synthesis," *Journal of bone and mineral research*, vol. 15, no. 4, pp. 721-739, 2000.

L. Melton III, E. Atkinson, C. Cooper, W. O'Fallon, and B. Riggs, "Vertebralfractures predict subsequent fractures," *Osteoporosis International*, vol. 10, no. 3, pp. 214-221, 1999.

M. Nevitt, B. Ettinger, D. Black, K. Stone, S. Jamal, K. Ensrud, M. Segal, H. Genant, and S. Cummings, "The association of radiographically detected vertebral fractures with back pain and function: a prospective study."

P. Lips, C. Cooper, D. Agnusdei, F. Caulin, P. Egger, O. Johnell, J. Kanis, S. Kellingray, A. Leplege, U. Liberman, E. McCloskey, H. Minne, J. Reeve, J. Reginster, M. Scholz, C. Todd, and M. de Vernejoul, "Quality of life in patients with vertebral fractures: validation of the quality of life questionnaire of the european foundation for osteoporosis (qualeffo). working party for quality of life of the european foundation for osteoporosis."

S. Pluijm, M. Dik, C. Jonker, D. Deeg, G. Van Kamp, and P. Lips, "Effects of gender and age on the association of apolipoprotein e $_{\varepsilon}$4 with bone mineral density, bone turnover and the risk of fractures in older people," *Osteoporosis International*, vol. 13, no. 9, pp. 701-709, 2002.

F. Alambeigi, M. Bakhtiarinejad, S. Sefati, R. Hegeman, I. Iordachita, H. Khanuja, and M. Armand, "On the use of a continuum manipulator and a bendable medical screw for minimally invasive interventions in orthopedic surgery," *IEEE transactions on medical robotics and bionics*, vol. 1, no. 1, pp. 14-21, 2019.

F. Shweikeh, J. P. Amadio, M. Arnell, Z. R. Barnard, T. T. Kim, J. P. Johnson, and D. Drazin, "robotics and the spine: a review of current and ongoing applications," *Neurosurgical Focus*, vol. 36, no. 3, p. E10, 2014.

C. L. Goldstein, D. S. Brodke, and T. J. Choma, "Surgical management of spinal conditions in the elderly osteoporotic spine," *Neurosurgery*, vol. 77, no. suppl 1, pp. S98-S107, 2015.

T. M. Shea, J. Laun, S. A. Gonzalez-Blohm, J. J. Doulgeris, W. E. Lee 3rd, K. Aghayev, and F. D. Vrionis, "Designs and techniques that improve the pullout strength of pedicle screws in osteoporotic vertebrae: current status," *BioMed research international,* 2014.

F. Alambeigi, "Dexterity and autonomy in minimally invasive surgical robotics intervention," Ph.D. dissertation, John Hopkins University, 2019.

N. Ordway, M. Wilson, T. Buerkle, E. Seybold, and H. Yuan, "Lumbar pedicle screw fixation in osteoporotic bone: A technique utilizing pmma and a fenestrated screw," 51*st Annual Meeting of the Orthopaedic Research Society,* 2005.

S. Sharma, T. G. Mohanraj, J. P. Amadio, M. Khadem, and F. Alambeigi, "A steerable drilling robot for minimally invasive spinal fixation of osteoporotic vertebrae."

F. Alambeigi, M. Bakhtiarinejad, A. Azizi, R. Hegeman, I. Iordachita, H. Khanuja, and M. Armand, "Inroads toward robot-assisted internal fixation of bone fractures using a bendable medical screw and the curved drilling technique," in 2018 7*th IEEE International Conference on Biomedical Robotics and Biomechatronics* (*Biorob*). IEEE, 2018, pp. 595-600.

M. Tilton, G. S. Lewis, H. B. Wee, A. Armstrong, M. W. Hast, and G. Manogharan, "Additive manufacturing of fracture fixation implants: Design, material characterization, biomechanical modeling and experimentation," *Additive Manufacturing*, vol. 33, 2020.

R. Feng, "Material characterization of additive manufactured metals using a line-focus transducer system," Master's thesis, University of Pittsburgh, 2021. *EOS StainlessSteel* 316*L*, EOS, 2014.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A U-bridge implant device comprising:

a length extending between a proximal end and a distal end;

a driving head at the proximal end;

a mating connector at the distal end; and a flexible engagement member having a length and positioned between the driving head and the mating connector, the flexible engagement member being bendable along its length;

wherein the flexible engagement member comprises a load-bearing structure configured to undergo distributed bending along at least a portion of its length such that the implant device is capable of conforming to a curved trajectory within a bone;

wherein the distributed bending along its length increases towards the distal end; and wherein the mating connector is configured to fixedly engage a mating connector of a second U-bridge implant device.

2. The implant device of claim 1, wherein the flexible engagement member is attached to the driving head at the proximal end and the mating connector at the distal end, such that the engagement member extends for the length of the implant device.

3. The implant device of claim 1, wherein the driving head is attached to a shank that extends towards the distal end for a portion of the length of the implant device.

4. The implant device of claim 3, wherein the length of the implant device comprising the shank is rigid.

5. The implant device of claim 3, wherein the flexible engagement member attaches to an exterior of the shank for at least a portion of a length of the shank.

6. The implant device of claim 3, wherein the flexible engagement member extends from the shank at a proximal end and is attached to the mating connector at a distal end.

7. The implant device of claim 1, wherein the mating connector is selected from the group consisting of: a push lock fitting, a threaded connector, and a magnet.

8. The implant device of claim 1, wherein the flexible engagement member comprises a variable cross-sectional shape.

9. The implant device of claim 8, wherein the cross-sectional shape is selected from the group consisting of: a triangle shape, a square shape, a pentagon shape, a hexagon shape, a rectangular shape, a rhombus shape, a diamond shape, and a trapezoid shape.

10. The implant device of claim 1, wherein the flexible engagement member has an outer diameter that is variable along the length of the engagement member.

11. The implant device of claim 1, wherein the flexible engagement member has an inner diameter that is variable along the length of the engagement member.

12. The implant device of claim 1, wherein the flexible engagement member comprises an engagement structure on an outer-facing surface selected from the group consisting of: a screw thread, a knurling pattern, a grating pattern, and combinations thereof.

13. The implant device of claim 12, wherein the screw thread has a thread pitch that is variable along the length of the screw thread.

* * * * *